(12) United States Patent
Parihar et al.

(10) Patent No.: US 8,460,206 B2
(45) Date of Patent: Jun. 11, 2013

(54) MULTI-ORIENTATION TARGETING SET FOR MRI BIOPSY DEVICE

(75) Inventors: Shailendra K. Parihar, Mason, OH (US); Jessica P. Leimbach, Cincinnati, OH (US); Michael R. Ludzack, Maineville, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 1136 days.

(21) Appl. No.: 12/337,872

(22) Filed: Dec. 18, 2008

(65) Prior Publication Data
US 2010/0160810 A1 Jun. 24, 2010

(51) Int. Cl.
*A61B 10/00* (2006.01)
(52) U.S. Cl.
USPC ............ 600/567; 600/562; 600/564; 600/566
(58) Field of Classification Search
USPC .................................................. 600/562–572
See application file for complete search history.

(56) References Cited

U.S. PATENT DOCUMENTS

| | | | |
|---|---|---|---|
| 5,526,822 A | 6/1996 | Burbank et al. | |
| 6,086,544 A | 7/2000 | Hibner et al. | |
| 6,626,849 B2 | 9/2003 | Huitema et al. | |
| 6,889,073 B2 * | 5/2005 | Lampman et al. | 600/422 |
| 7,442,171 B2 | 10/2008 | Stephens et al. | |
| 7,507,210 B2 | 3/2009 | Hibner et al. | |
| 7,708,751 B2 | 5/2010 | Hughes et al. | |
| 7,831,290 B2 | 11/2010 | Hughes et al. | |
| 2003/0199753 A1 | 10/2003 | Hibner et al. | |
| 2003/0199785 A1 | 10/2003 | Hibner et al. | |
| 2005/0159677 A1 | 7/2005 | Shabaz et al. | |
| 2005/0277829 A1 | 12/2005 | Tsonton et al. | |
| 2006/0258956 A1 | 11/2006 | Haberstich et al. | |
| 2007/0167736 A1 | 7/2007 | Dietz et al. | |
| 2008/0195066 A1 | 8/2008 | Speeg et al. | |
| 2008/0214955 A1 | 9/2008 | Speeg et al. | |

FOREIGN PATENT DOCUMENTS

| | | |
|---|---|---|
| EP | 1 356 773 | 10/2003 |
| EP | 1 604 615 | 12/2005 |
| EP | 1 859 742 | 11/2007 |

OTHER PUBLICATIONS

International Preliminary Report on Patentability dated Jun. 21, 2011 for Application No. PCT/US2009/067308.
International Search Report dated May 3, 2010 for Application No. PCT/US2009/067308.

(Continued)

*Primary Examiner* — Rene Towa
*Assistant Examiner* — Adam Eiseman
(74) *Attorney, Agent, or Firm* — Frost Brown Todd LLC

(57) ABSTRACT

A biopsy device targeting set includes a vertical member, a carriage that is vertically movable along the vertical member, and a cradle coupled with the carriage. The cradle has a pair of substantially perpendicular mounting arms. Each mounting arm has a recess that may receive a rail of the carriage, such that the cradle may be mounted to the same rail in different orientations. Each mounting arm also has a biopsy device mounting feature, which may be a recess or a rail. The biopsy device mounting feature is configured to engage with a complementary feature of a biopsy device, such that a biopsy device may be mounted to either mounting arm. A z-stop feature is operable to selectively restrict longitudinal motion along either or both of the biopsy device mounting features. The targeting set may be used with a biopsy device in an MRI environment.

13 Claims, 35 Drawing Sheets

OTHER PUBLICATIONS

International Preliminary Report on Patentability dated Jun. 21, 2011 for Application No. PCT/US2009/067346.
International Search Report dated Feb. 19, 2010 for Application No. PCT/US2009/067346.
International Preliminary Report on Patentability dated Jun. 21, 2011 for Application No. PCT/US2009/067355.
International Search Report dated Feb. 26, 2010 for Application No. PCT/US2009/067355.

U.S. Appl. No. 12/337,674, Dec. 18, 2008, Parihar et al.
U.S. Appl. No. 12/337,785, Dec. 18, 2008, Parihar et al.
U.S. Appl. No. 12/337,814, Dec. 18, 2008, Parihar et al.
U.S. Appl. No. 12/337,874, Dec. 18, 2008, Parihar et al.
U.S. Appl. No. 12/337,911, Dec. 18, 2008, Parihar et al.
U.S. Appl. No. 12/337,942, Dec. 18, 2008, Parihar et al.
U.S. Appl. No. 60/869,736, Dec. 13, 2006, Ritchie et al.
U.S. Appl. No. 60/874,792, Dec. 13, 2006, Hibner et al.

* cited by examiner

MULTI-ORIENTATION TARGETING SET FOR MRI BIOPSY DEVICE

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," filed Nov. 20, 2007; U.S. Provisional Patent Application Ser. No. 60/869,736, entitled "Biopsy System," filed Dec. 13, 2006; U.S. Provisional Patent Application Ser. No. 60/874,792, entitled "Biopsy Sample Storage," filed Dec. 13, 2006; and U.S. Pub. No. 2008/0195066, entitled "Revolving Tissue Sample Holder For Biopsy Device," published Aug. 14, 2008. The disclosure of each of the above-cited U.S. Patents, U.S. Patent Application Publications, and U.S. Provisional Patent Applications is incorporated by reference herein.

BACKGROUND

Some biopsy systems may provide a probe assembly having an attached or integral needle. Such biopsy systems may also be used with a separate targeting cannula and obturator, which are used to create the channel through the tissue to a desired biopsy site. In some such biopsy systems, the obturator may be removed once the cannula is positioned in tissue, and the needle of the probe assembly may be inserted through the cannula to reach the biopsy site. The tissue sample may then be pulled through aligning apertures in the cannula and needle into an axial lumen of the needle. A cutter may then travel through the axial lumen to sever the tissue sample, which may be communicated proximally through a lumen defined by the cutter.

In some other biopsy systems, a probe assembly may have a cutter but lack an integral needle. For instance, a detachable needle may serve same the functions that would otherwise be served by two separate components—a targeting cannula and a needle—as noted above. In some such systems, the detachable needle may be used with an obturator to create a channel through tissue to a desired biopsy site. The obturator may be removed once the detachable needle is positioned within the tissue, and the probe assembly may be coupled with the detachable needle. The cutter may be translated through the axial lumen of the needle to sever a tissue sample from tissue protruding through a transverse aperture formed in the needle. The tissue sample may then be communicated proximally through a lumen defined by the cutter.

Regardless of whether a detachable needle or integral needle with separate cannula is used, it may be desirable to provide some degree of guidance and/or fixation for such a detachable needle or for such a cannula that is separate from a needle that is integral with a biopsy probe.

While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

DETAILED DESCRIPTION

Figure 1:
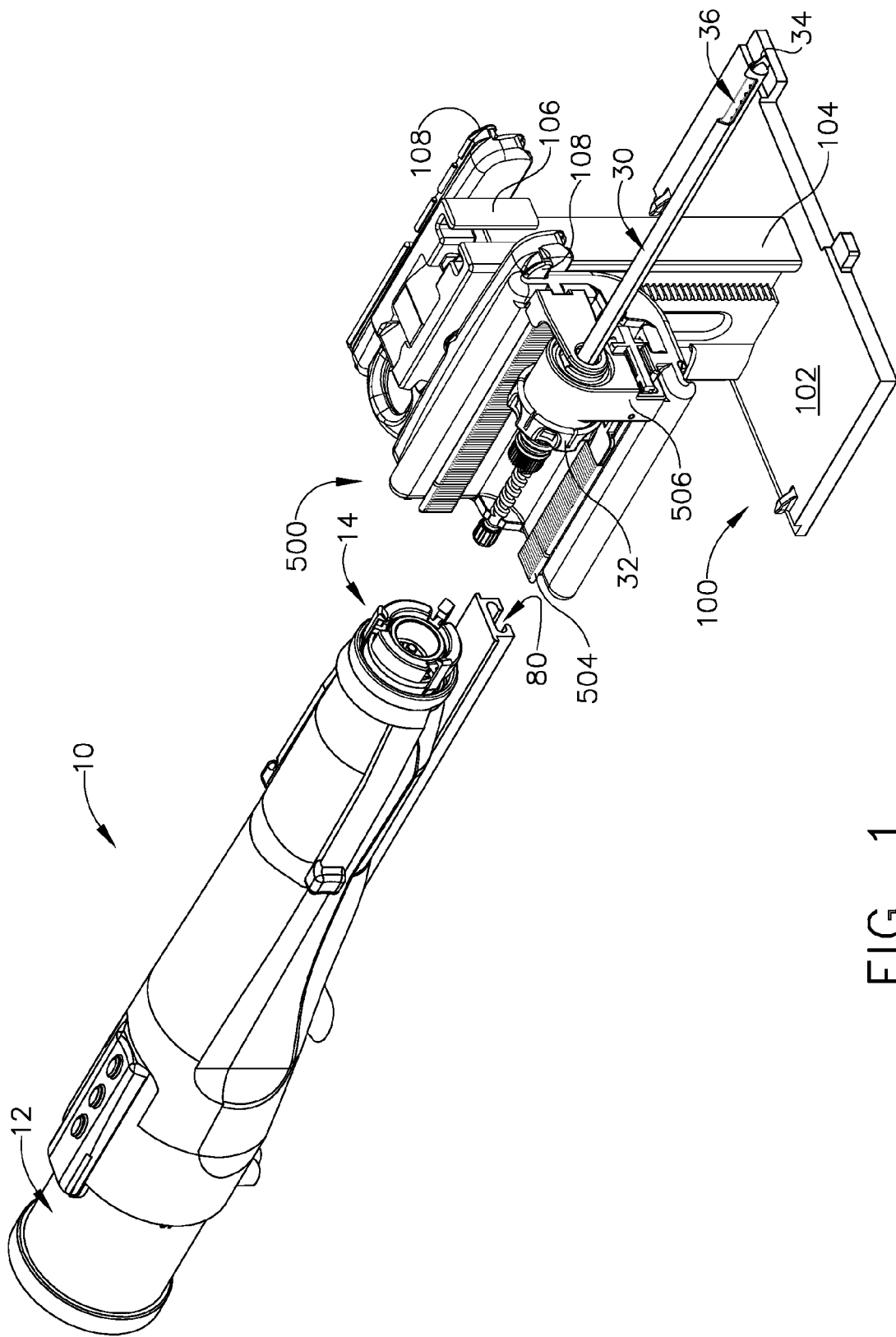
FIG. 1 depicts a perspective view of an exemplary biopsy system targeting set and an exemplary biopsy device.

The following description of certain examples should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview of Exemplary Biopsy Device and Targeting Systems

Examples described herein relate to the acquisition of tissue samples from a patient's breast with assistance of MRI imaging. It should be understood, however, that various examples described herein may be used to acquire tissue samples from various other locations on or in a patient. Similarly, it should be understood that examples described herein may be used in combination with any other suitable imaging modality, including but not limited to x-ray, ultrasound, PEM, BSGI, or any other suitable imaging modality, if not combinations of various imaging modalities.

Examples described herein refer to certain biopsy devices (10, 50, 75), certain aspects of which will be described in greater detail below. However, it should be understood that any other suitable biopsy device may be incorporated into the exemplary systems, devices, and methods of use described herein, and vice versa. By way of example only, examples described herein may be used with any biopsy device or other component described in U.S. Non-Provisional patent application Ser. No. 12/337,874entitled "MECHANICAL TISSUE SAMPLE HOLDER INDEXING DEVICE," filed on even date herewith, the disclosure of which is incorporated by reference herein; U.S. Non-Provisional patent application Ser. No. 12/337,674, entitled "BIOPSY DEVICE WITH SLIDING CUTTER COVER," filed on even date herewith, the disclosure of which is incorporated by reference herein; U.S. Non-Provisional patent application Ser. No. 12/337,911, entitled "BIOPSY DEVICE WITH DISCRETE TISSUE CHAMBERS," filed on even date herewith, the disclosure of which is incorporated by reference herein; U.S. Non-Provisional patent application Ser. No. 12/337,942, entitled "TISSUE BIOPSY DEVICE WITH CENTRAL THUMBWHEEL," filed on even date herewith, the disclosure of which is incorporated by reference herein; or U.S. Pub. No. 2008/0195066, entitled "Revolving Tissue Sample Holder For Biopsy Device," published Aug. 14, 2008, the disclosure of which is incorporated by reference herein. Still other suitable biopsy devices or other components that may be used with examples described herein will be apparent to those of ordinary skill in the art in view of the teachings herein.

It should also be understood that systems, devices, components, and methods of use herein may be incorporated into a variety of structural and methodological settings. By way of example only, any suitable teaching of U.S. Pub. No. 2005/0277829, entitled "MRI BIOPSY APPARATUS INCORPORATING A SLEEVE AND A MULTI-FUNCTION OBTURATOR," published Dec. 15, 2005, the disclosure of which is incorporated by reference herein, may be incorporated into any of the present examples; or any of the teachings herein may be incorporated into any of the examples disclosed in that U.S. Patent Application Publication. Similarly, any suitable teaching of U.S. Pub. No. 2007/0167736, entitled "MRI BIOPSY APPARATUS INCORPORATING AN IMAGEABLE PENETRATING PORTION," published Jul. 19, 2007, the disclosure of which is incorporated by reference herein, may be incorporated into any of the present examples; or any of the teachings herein may be incorporated into any of the examples disclosed in that U.S. Patent Application Publication. Likewise, any suitable teaching of U.S. Pub. No. 2003/0199785, entitled "LOCALIZATION MECHANISM FOR AN MRI COMPATIBLE BIOPSY DEVICE," published Oct. 23, 2003, the disclosure of which is incorporated by reference herein, may be incorporated into any of the present examples; or any of the teachings herein may be incorporated into any of the examples disclosed in that U.S. Patent Application Publication. As another merely illustrative example, any suitable teaching of U.S. Pub. No. 2007/0255170, entitled "BIOPSY CANNULA ADJUSTABLE DEPTH STOP," published Nov. 1, 2007, the disclosure of which is incorporated by reference herein, may be incorporated into any of the present examples; or any of the teachings herein may be incorporated into any of the examples disclosed in that U.S. Patent Application Publication. As yet another merely illustrative example, any suitable teaching of U.S. Pub. No. 2008/0195066, entitled "Revolving Tissue Sample Holder For Biopsy Device," published Aug. 14, 2008, the disclosure of which is incorporated by reference herein, may be incorporated into any of the present examples; or any of the teachings herein may be incorporated into any of the examples disclosed in that U.S. Patent Application Publication. Suitable ways in which teachings may be interchanged either way among any of the above-cited U.S. Patent Application Publications and the disclosure herein will be apparent to those of ordinary skill in the art in view of the disclosure herein.

While not shown, any biopsy device (10, 50, 75) described herein may be coupled with a vacuum control module. Such a vacuum control module may be used to provide vacuum, pressurized air, saline, venting, electrical power, mechanical rotary power (e.g., via a drive cable), control signals, or any other suitable provision to biopsy device (10, 50, 75). An exemplary vacuum control module and ways in which a vacuum control module may be used with a biopsy device (10, 50, 75) are disclosed in U.S. Pub. No. 2008/0195066, entitled "Revolving Tissue Sample Holder For Biopsy Device," published Aug. 14, 2008, the disclosure of which is incorporated by reference herein. It should also be understood that an interface may be provided between such a vacuum control module and biopsy device (10, 50, 75). For instance, such an interface may (or may not) be desired when biopsy device (10, 50, 75) will be used in an MRI setting. An example of such an interface that may be used with a vacuum control module and with biopsy device (10, 50, 75) is disclosed in U.S. Non-Provisional patent application Ser. No. 12/337,814, entitled "CONTROL MODULE INTERFACE," filed on even date herewith, the disclosure of which is incorporated by reference herein. Still other suitable devices and components that may be used with biopsy device (10, 50, 75) or with any other device or component described herein will be apparent to those of ordinary skill in the art in view of the teachings herein.

A. Exemplary Biopsy Probe with Detachable Needle and Targeting System

Figure 2:
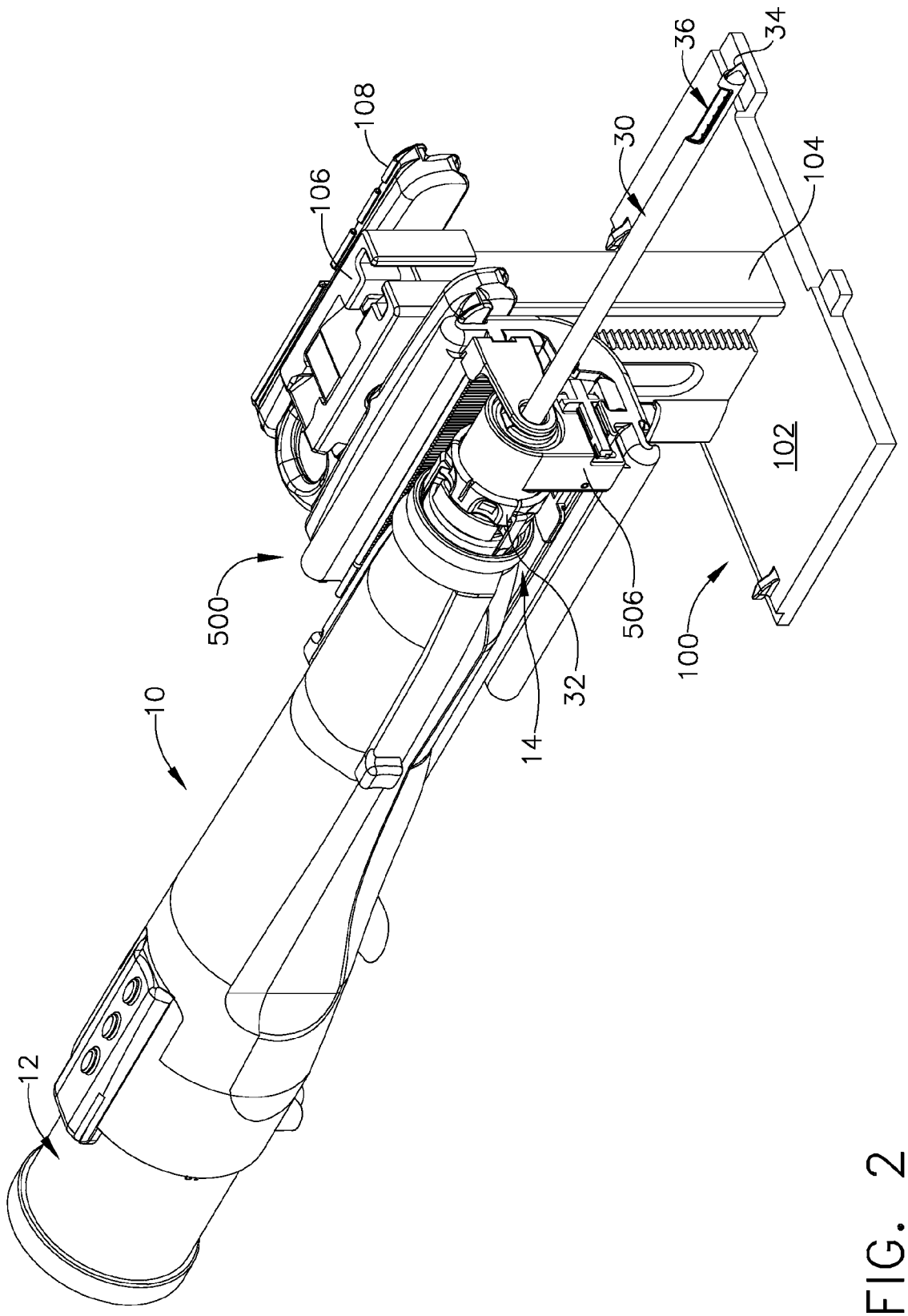
FIG. 2 depicts a perspective view of the biopsy device of FIG. 1 coupled with the targeting set of FIG. 1.

FIGS. 1-2 show an exemplary biopsy probe (10) that couples with a detachable needle (30). Needle (30) is coupled with a cradle (500), which is coupled with a targeting pedestal (100). Biopsy probe (10) has a tissue sample holder (12) at its proximal end and a needle engagement mechanism (14) at its distal end. Needle (30) has a thumbwheel (32) at its proximal end and an integral tissue piercing tip (34) at its distal end. Needle (30) also has a transverse tissue receiving aperture (36) proximal to tip (34). Needle engagement mechanism (14) is configured to releasably couple with thumbwheel (32), as shown in FIG. 2. Once this coupling is accomplished, a hollow cutter (not shown) within probe (10) may be advanced within a lumen defined by needle (30) to sever tissue protruding through aperture (36). The severed tissue sample may then be communicated proximally through a lumen defined by the cutter to reach tissue sample holder (12). Biopsy probe (10) and needle (30) may further be constructed and used in accordance with any of the teachings of U.S. Non-Provisional patent application Ser. No. 12/337,674, entitled "BIOPSY DEVICE WITH SLIDING CUTTER COVER," filed on even date herewith, the disclosure of which is incorporated by reference herein. Alternatively, biopsy probe (10) may have any other suitable features, components, configurations, functionalities, or methods of operation.

Pedestal (100) of the present example comprises a base (102), an upright member (104), and a carriage (106). Carriage (106) is movable vertically along upright member (104), and includes a ratcheting mechanism (not shown) to selectively secure the vertical position of carriage (106) relative to upright member (104). Rails (108) are mounted to either side of carriage (106). As shown, cradle (500) is configured to mount to carriage (106) by engaging rail (108). For instance, a recess (502) of cradle (500) may receive rail (108), as will be described in greater detail below, such that cradle (500) may be slid onto rail (108) and be removably secured thereto. By way of example only, pedestal (100) may comprise a conventional pedestal assembly (or any component thereof) that is part of a breast biopsy MRI guidance system by Invivo Corp. of Orlando, Fla. Of course, any other suitable type of pedestal (100) may be used.

Cradle (500) of the present example includes a pair of rails (504). A needle mount (506) is slidingly engaged with rail (504). Needle (30) is secured to needle mount (506). The longitudinal position of needle mount (506) along rail (504) may thus be adjusted to select a desired depth of insertion for needle (30). Additional aspects of cradle (500) will be described in greater detail below with reference to FIGS. 15-18, while other aspects of cradle (500) will be apparent to those of ordinary skill in the art in view of the teachings herein.

While cradle (500) is shown in this example as being used in conjunction with pedestal (100), it should be understood that any other cradle (200, 300, 400, 600, 700, 800) described herein may be used in conjunction with pedestal (100). Cradle (500) may also be used with some device or component other than pedestal (100), including but not limited to targeting grid assembly (150) described below. Similarly, any suitable biopsy device, including but not limited to any biopsy device described herein (10, 50, 75), may be used in conjunction with pedestal (100) and/or in conjunction with any cradle (200, 300, 400, 500, 600, 700, 800) described herein. Suitable combinations of any of these components will be apparent to those of ordinary skill in the art in view of the teachings herein.

B. Exemplary Biopsy Probe with Cannula and Targeting System

Figure 3:
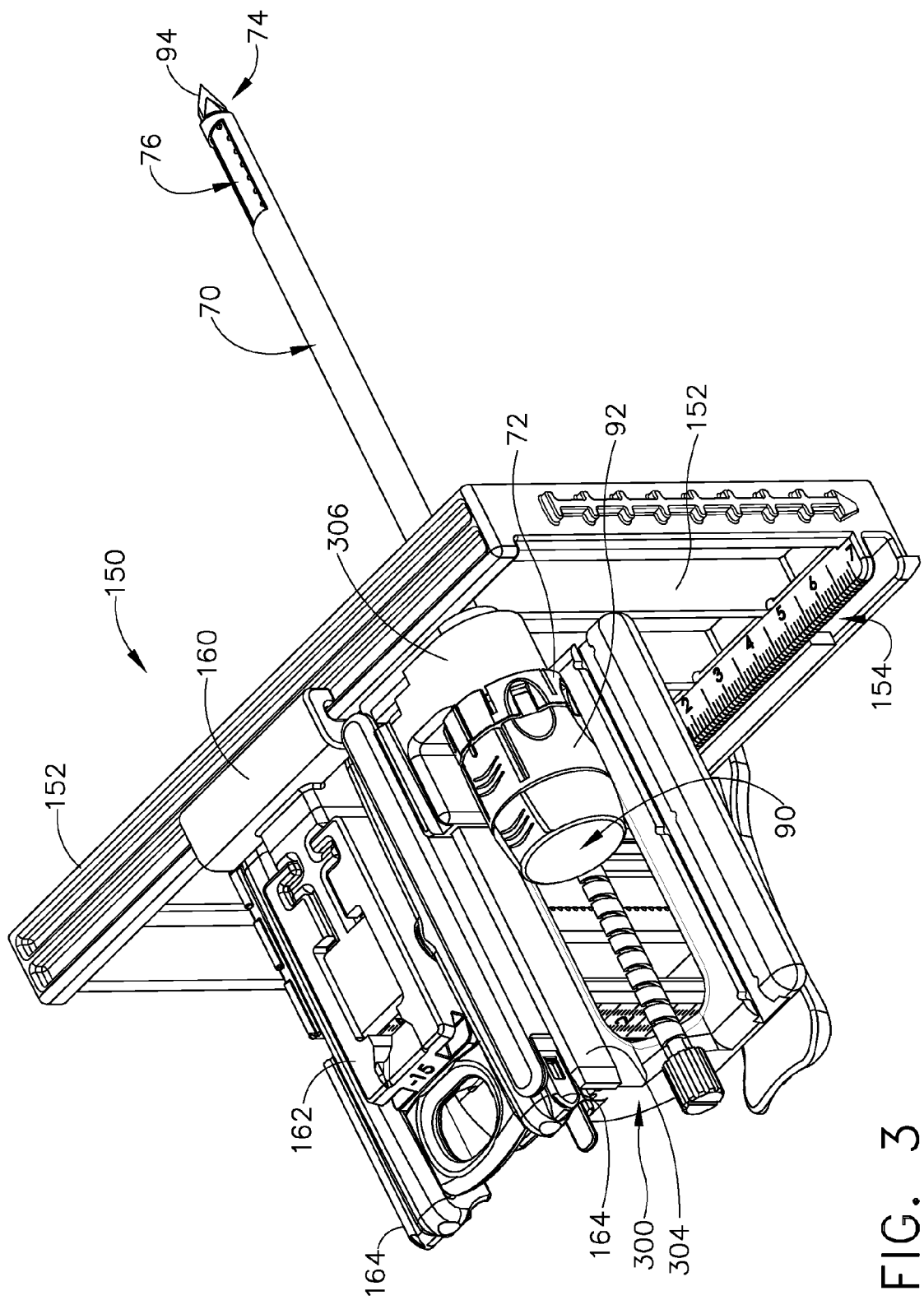
FIG. 3 depicts a perspective view of another exemplary biopsy system targeting set, with an obturator inserted in a targeting cannula.
Figure 4:
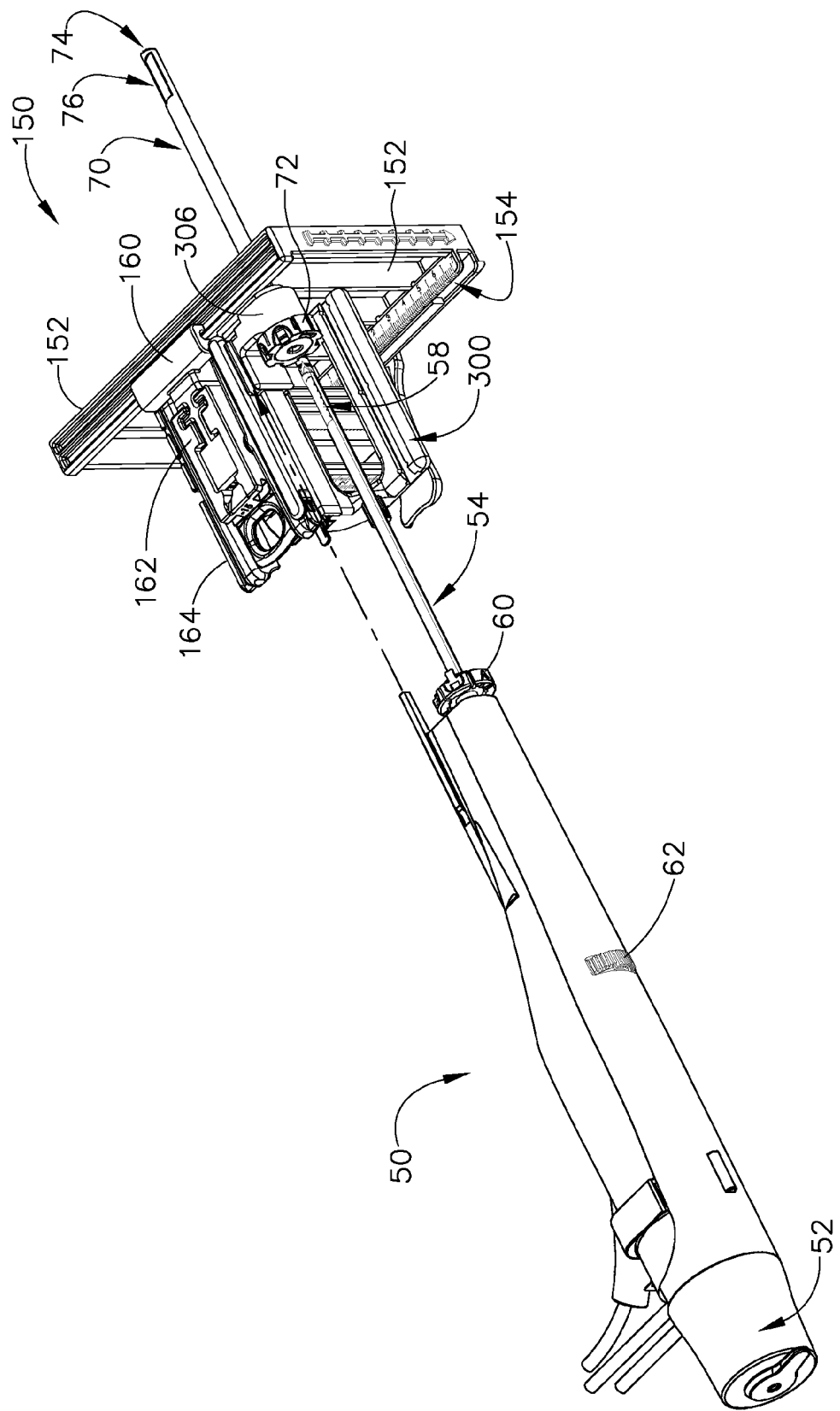
FIG. 4 depicts a perspective view of the targeting set of FIG. 3, with the obturator removed, and with a biopsy device staged for coupling with the targeting set.
Figure 5:
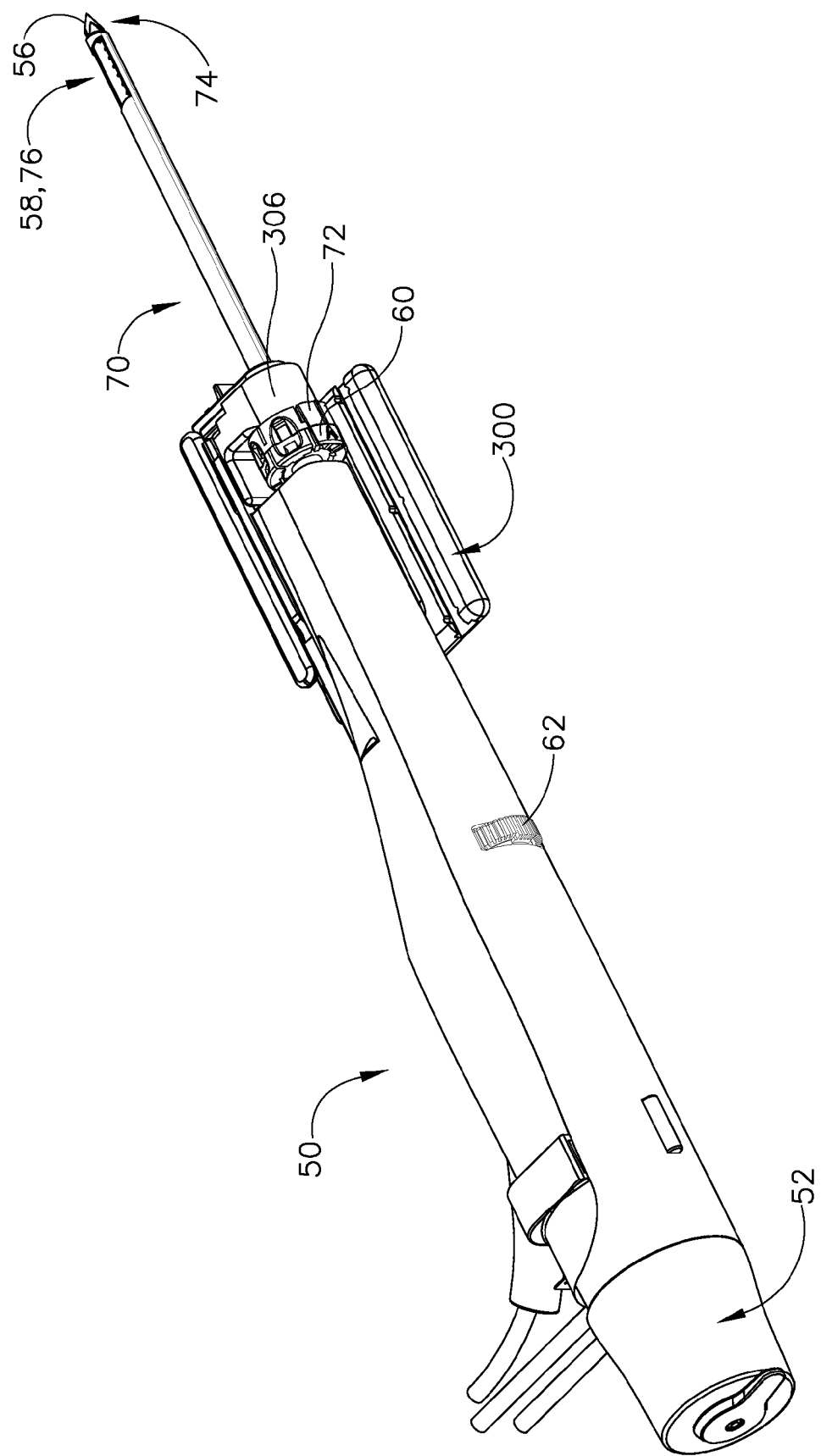
FIG. 5 depicts a perspective view of the targeting set of FIG. 3 with the biopsy device of FIG. 4 coupled thereto.

FIGS. 3-5 show another exemplary biopsy probe (50), which couples with a targeting cannula (70). An obturator (90) is also included in this example. Targeting cannula (70) is coupled with a cradle (300), which is coupled with a targeting grid assembly (150). Biopsy probe (50) has a tissue sample holder (52) at its proximal end and an integral needle (54) at its distal end. Needle (54) has a tip (56) at its distal end and a transverse tissue receiving aperture (58) proximal to tip (56). Tip (56) may be blunt, bladed, or have any other suitable features or properties. Biopsy probe (50) also has a distal thumbwheel (60) and a central thumbwheel (62), each of which is in communication with needle (54), and each of which is manually operable to rotate needle (54) about a longitudinal axis defined by needle (54). Such rotation may be used to selectively orient aperture (58) at a desired angular position about the longitudinal axis.

Targeting cannula (70) has a thumbwheel (72) at its proximal end and an opening (74) at its distal end. Targeting cannula (70) also has a transverse tissue receiving aperture (76) proximal to opening (74). Thumbwheel (72) is manually operable to rotate targeting cannula (70) about a longitudinal axis defined by targeting cannula (70). Such rotation may be used to selectively orient aperture (76) at a desired angular position about the longitudinal axis. Furthermore, thumbwheel (72) is configured to couple with distal thumbwheel (60) of biopsy probe (50) when biopsy probe (50) is coupled with targeting cannula (70) as described in greater detail below with reference to FIG. 5. When thumbwheel (72) is coupled with distal thumbwheel (60), thumbwheels (60, 72) may rotate unitarily together. Any thumbwheel (60, 62, 72) may be manually rotated to concomitantly rotate needle (54) and cannula (70) about a common longitudinal axis, such as to selectively orient apertures (58, 76) at a desired angular position about the longitudinal axis.

As shown in FIGS. 3-5, targeting cannula (70) is configured to selectively receive obturator (90) or needle (54). Obturator (90) has a grip (92) at its proximal end and an integral tissue piercing tip (94) at its distal end. As shown in FIG. 3, obturator (90) is configured to fit within targeting cannula (70), such that tissue piercing tip (94) of obturator (90) protrudes through distal opening (74) of targeting cannula (70). By way of example only, obturator (90) and targeting cannula (70) may together be inserted into a patient's breast. Obturator (90) may then be withdrawn from targeting cannula (70), as shown in FIG. 4. Needle (54) may then be inserted into targeting cannula (70), as shown in FIG. 5, such that transverse aperture (58) of needle (54) substantially aligns with transverse aperture (76) of targeting cannula (70). Of course, needle (54) and/or targeting cannula (70) may be rotated (e.g., by manually rotating a thumbwheel (60, 62, 72)) before needle (54) is inserted into targeting cannula (70), such as to align apertures (58, 76) at a common angular position about the common longitudinal axis before thumbwheel (72) is coupled with distal thumbwheel (60).

Once needle (54) is inserted in targeting cannula (70), and apertures (58, 76) are oriented at the desired angular position, a hollow cutter (not shown) within probe (50) may be advanced within a lumen defined by needle (54) to sever tissue protruding through apertures (58, 76). The severed tissue sample may then be communicated proximally through a lumen defined by the cutter to reach tissue sample holder (52), such as under the influence of a vacuum and/or pressurized air. Biopsy probe (50) and needle (54) may further be constructed and used in accordance with any of the teachings of U.S. Non-Provisional patent application Ser. No. 12/337,942, entitled "TISSUE BIOPSY DEVICE WITH CENTRAL THUMBWHEEL," filed on even date herewith, the disclosure of which is incorporated by reference herein. Alternatively, biopsy probe (50) may have any other suitable features, components, configurations, functionalities, or methods of operation.

Targeting grid assembly (150) of the present example comprises a grid (152) and a mount (160) coupled with grid (152). Grid (152) comprises a plurality of vertical slats (152), vertical positioning indicia (153), and horizontal positioning indicia (154). Mount (160) is operable to translate horizontally across grid (152). Indicia (154) may assist in positioning mount (160) at an appropriate horizontal location. A carriage (162) is movable vertically along mount (160), and includes a ratcheting mechanism (not shown) to selectively secure the vertical position of carriage (162) relative to mount (160). Indicia (153) may assist in positioning carriage (162) at an appropriate vertical location. Rails (164) are mounted to either side of carriage (162). As shown, cradle (300) is configured to mount to carriage (162) by engaging rail (164). For instance, a recess (302) of cradle (300) may receive rail (164), as will be described in greater detail below, such that cradle (300) may be slid onto rail (164) and be removably secured thereto. By way of example only, targeting grid assembly (150) may comprise a conventional targeting grid assembly (or any component thereof) that is part of a breast biopsy MRI guidance system, including a breast coil, by Invivo Corp. of Orlando, Fla. Of course, any other suitable type of targeting grid assembly (150) may be used.

Cradle (300) of the present example includes a rail (304). A cannula mount (306) is slidingly engaged with rail (304). Cannula (70) is secured to cannula mount (306). The longitudinal position of cannula mount (306) along rail (304) may thus be adjusted to select a desired depth of insertion for cannula (70). Additional aspects of cradle (300) will be described in greater detail below with reference to FIGS. 7-10, while other aspects of cradle (300) will be apparent to those of ordinary skill in the art in view of the teachings herein.

While cradle (300) is shown in this example as being used in conjunction with targeting grid assembly (150), it should be understood that any other cradle (200, 400, 500, 600, 700, 800) described herein may be used in conjunction with targeting grid assembly (150). Cradle (300) may also be used with some device or component other than targeting grid assembly (150), including but not limited to pedestal (100) described above. Similarly, any suitable biopsy device, including but not limited to any biopsy device described herein (10, 50, 75), may be used in conjunction with targeting grid assembly (150) and/or in conjunction with any cradle (200, 300, 400, 500, 600, 700, 800) described herein. Suitable combinations of any of these components will be apparent to those of ordinary skill in the art in view of the teachings herein.

II. Exemplary Engagement Between Biopsy Probe and Targeting Cradle

While several examples of cradles (200, 300, 400) will be discussed below in the context of targeting cannulas (70) and biopsy devices (50) that have an integral needle (54), it should be understood that cradles (200, 300, 400) may also be used with detachable needles (30) and biopsy devices (10) that lack an integral needle (54). Furthermore, it should be understood that any of the below described cradles (200, 300, 400) may be subject to any desired addition, omission, variation, modification, substitution, supplementation, or method of use.

A. Exemplary Modular Cradle

Figure 6:
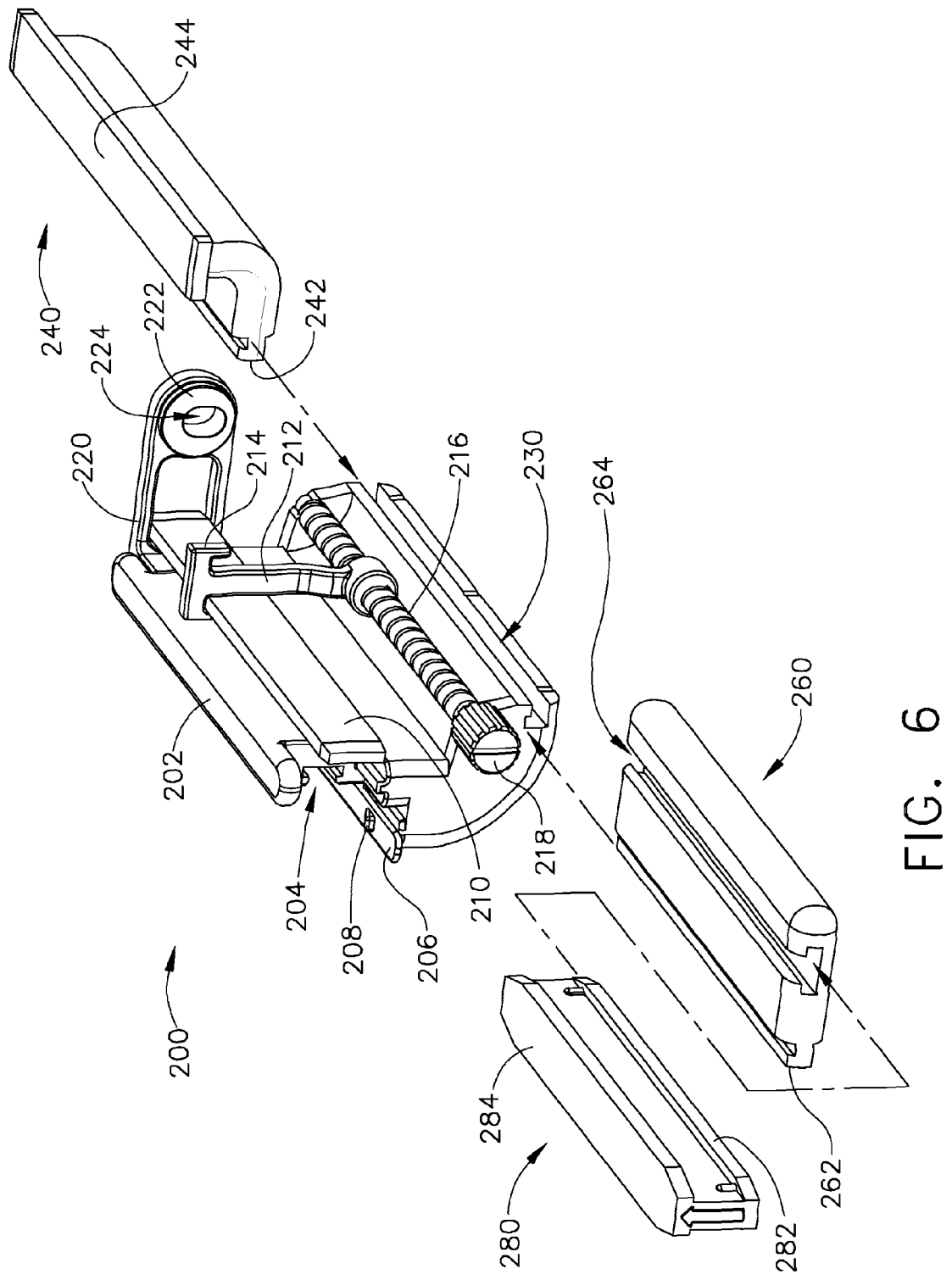
FIG. 6 depicts a perspective view of an exemplary cradle assembly for a biopsy device targeting set, with various biopsy device coupling adapters.

FIG. 6 shows an exemplary modular cradle (200). Cradle (200) includes a base member (202), which is configured to couple with various adapters (240, 260, 280). Base member (202) includes a recess (204), which may slidingly engage a rail (108, 164) of pedestal (100), targeting grid assembly (150), or any other structure. A resilient arm (206) extends adjacent to recess (204), and includes a protrusion (208) that is configured to selectively secure base member (202) relative to rail (108, 164). For instance, an operator may slide rail (108, 164) into recess (204), and protrusion (208) may deflect away from rail (108, 164) then "snap" into a complementary recess (not shown) formed in rail (108, 164), such that protrusion (208) and the recess formed in rail (108, 164) restrict longitudinal motion of base member (202) relative to rail (108, 164). To remove base member (202) from rail (108, 164), an operator may simply depress arm (206) to disengage protrusion (208) from the recess formed in rail (108, 164), and pull base member (202) away from rail (108, 164). Of course, any other suitable components, features, or configurations may be used to selectively secure base member (202) relative to rail (108, 164).

Base member (202) also presents a rail (210), with which a cannula mount (306), needle mount (506), and/or biopsy device (10, 50) may be engaged. Rail (210) has a protruding "T" cross-section in this example, though it will be appreciated that any other suitable configuration may be used (e.g., dovetail, etc.). Furthermore, rail (210) may be substituted or supplemented with a "T"-shaped (or otherwise shaped) recess (not shown), which may be configured to receive a complementary rail (not shown) of a cannula mount (306), needle mount (506), and/or biopsy device (10, 50). In the present example, base member (202) also includes a z-stop (212), which has opposing rail engagement members (214). Z-stop (212) is coupled with a screw gear (216), which has a rotation knob (218). It will be appreciated that an operator may manually rotate rotation knob (218) to selectively position z-stop (212) along the length of screw gear (216). As shown, one of rail engagement members (214) is engaged with rail (210). Such engagement may prevent z-stop (212) from rotating as screw gear (216) is rotated to translate z-stop (212) along screw gear (216).

By way of example only, z-stop (212) may be used to control the depth at which a needle (30) or combined obturator (90) and targeting cannula (70) may be inserted into a patient. For instance, before coupling a cannula mount (306), needle mount (506), and/or biopsy device (10, 50) with rail (210), an operator may rotate knob (218) to set z-stop (212) at a desired longitudinal position along screw gear (216). The operator may then slide a cannula mount (306), needle mount (506), or biopsy device (10, 50) along rail (210) until a cannula mount (306), needle mount (506), or biopsy device (10, 50) engages z-stop (212), which may prevent a cannula mount (306), needle mount (506), or biopsy device (10, 50) from being advanced any further. Other mechanisms that may be used to restrict longitudinal movement of a cannula mount (306), needle mount (506), and/or biopsy device (10, 50) will be described in greater detail below, while other suitable alternatives will be apparent to those of ordinary skill in the art in view of the teachings herein.

A support member (220) is also secured to the distal end of base member (202). Support member (220) includes a bushing (222), which defines an opening (224) configured to receive needle (30) or targeting cannula (70). To the extent that needle (30) or targeting cannula (70) has a non-circular cross-section, opening (224) may be shaped to accommodate such a cross-section. Furthermore, bushing (222) may be rotatable within support member (220), such that bushing (222) may be rotated to accommodate needle (30) or targeting cannula (70) during insertion of needle (30) or targeting cannula (70) through opening (224); and to rotate with needle (30) or targeting cannula (70) after needle (30) or targeting cannula (70) has been inserted through opening (224). Support member (220) may provide additional support to a needle (30) or targeting cannula (70) that is coupled with support member (220). For instance, support member (220) may reduce deflection of needle (30) or targeting cannula (70) when z-stop (212) (and, hence, cannula mount (306) or needle mount (506)) is positioned relatively far from support member (220). Such reduction in deflection may be particularly desirable if an operator is attempting to insert a needle (30) or combined obturator (90) and targeting cannula (70) along a straight line into dense tissue. In some versions, support member (220) is rigidly secured to base member (202). In some other versions, support member (220) is configured to selectively pivot relative to base member (202) (e.g., to pivot it out of the way if z-stop (212) is advanced to a distal-most position). Of course, as with other components described herein, support member (220) is merely optional.

Base member (202) also has an adapter recess (230) in this example. Adapter recess (230) has a "L" shape, though it will be understood that recess (230) may have any other suitable shape. Adapter recess (230) is configured to receive a complementary rail (242, 262) of a selected adapter (240, 260). Adapter (240) presents a mounting rail (244), with which a cannula mount (306), needle mount (506), and/or biopsy device (10, 50) may be engaged. For instance, with adapter (240) coupled with base member (202), size/spacing considerations or other considerations might make rail (244) more ideal for mounting a cannula mount (306), needle mount (506), and/or biopsy device (10, 50) than rail (210) would be. While rail (244) has a "T" shaped cross-section in this example, it should be understood that any other suitable cross-sectional configuration may be used.

Z-stop (212) may still be operated to restrict longitudinal movement of a cannula mount (306), needle mount (506), and/or biopsy device (10, 50) along rail (244). For instance, the left rail engagement member (214) may still be engaged with rail (210) during such use. Alternatively, the left rail engagement member (214) may be disengaged from rail (210), then z-stop (212) may be rotated about screw gear (216) to engage the right rail engagement member (214) with rail (244). Other ways in which adapter (240) may be used will be apparent to those of ordinary skill in the art in view of the teachings herein.

As noted above, adapter (260) also has a rail (262) that may be slid into recess (230) of base member (202). Adapter (260) provides its own recess (264), with which a cannula mount (306), needle mount (506), and/or biopsy device (10, 50) may be engaged. For instance, some versions of a cannula mount (306), needle mount (506), and/or biopsy device (10, 50) may present a recess that complements rails (210, 244); while other versions of a cannula mount (306), needle mount (506), and/or biopsy device (10, 50) may present a rail that complements recess (264). Another exemplary use of recess (264) may include coupling with a complementary rail (282) of adapter (280). Adapter (280) may also present a mounting rail (284), with which a cannula mount (306), needle mount (506), and/or biopsy device (10, 50) may be engaged. Adapter (260) and/or the combination of adapter (260) with adapter (280) may thus be used in ways similar to those described above with respect to adapter (240). Of course, other suitable uses for adapters (240, 260, 280), as well as other suitable configurations for and combinations of adapters (240, 260, 280), will be apparent to those of ordinary skill in the art in view of the teachings herein.

While exemplary features, components, configurations, and methods of operation for cradle (200) have been described above, it should be understood that any suitable alternatives may be used. Suitable alternative features, components, configurations, and methods of operation for cradle (200) will be apparent to those of ordinary skill in the art in view of the teachings herein.

B. Exemplary Cradle with Slot Mounting

FIGS. 7-10 depict another exemplary cradle (300), along with an exemplary targeting cannula (70). Cradle (300) of this example includes unitary support arms (310, 320) that are substantially perpendicular to each other. Each support arm (310, 320) has a recess (302), which may slidingly engage a rail (108, 164) of pedestal (100), targeting grid assembly (150), or any other structure. A resilient arm (307) extends adjacent to recess (302), and includes a protrusion (308) that is configured to selectively secure cradle (300) relative to rail (108, 164). For instance, an operator may slide rail (108, 164) into either recess (302), and protrusion (308) may deflect away from rail (108, 164) then "snap" into a complementary recess (not shown) formed in rail (108, 164), such that protrusion (308) and the recess formed in rail (108, 164) restrict longitudinal motion of cradle (300) relative to rail (108, 164). To remove cradle (300) from rail (108, 164), an operator may simply lift arm (307) to disengage protrusion (308) from the recess formed in rail (108, 164), and pull cradle (300) away from rail (108, 164). Of course, any other suitable components, features, or configurations may be used to selectively secure cradle (300) relative to rail (108, 164).

Figure 7:
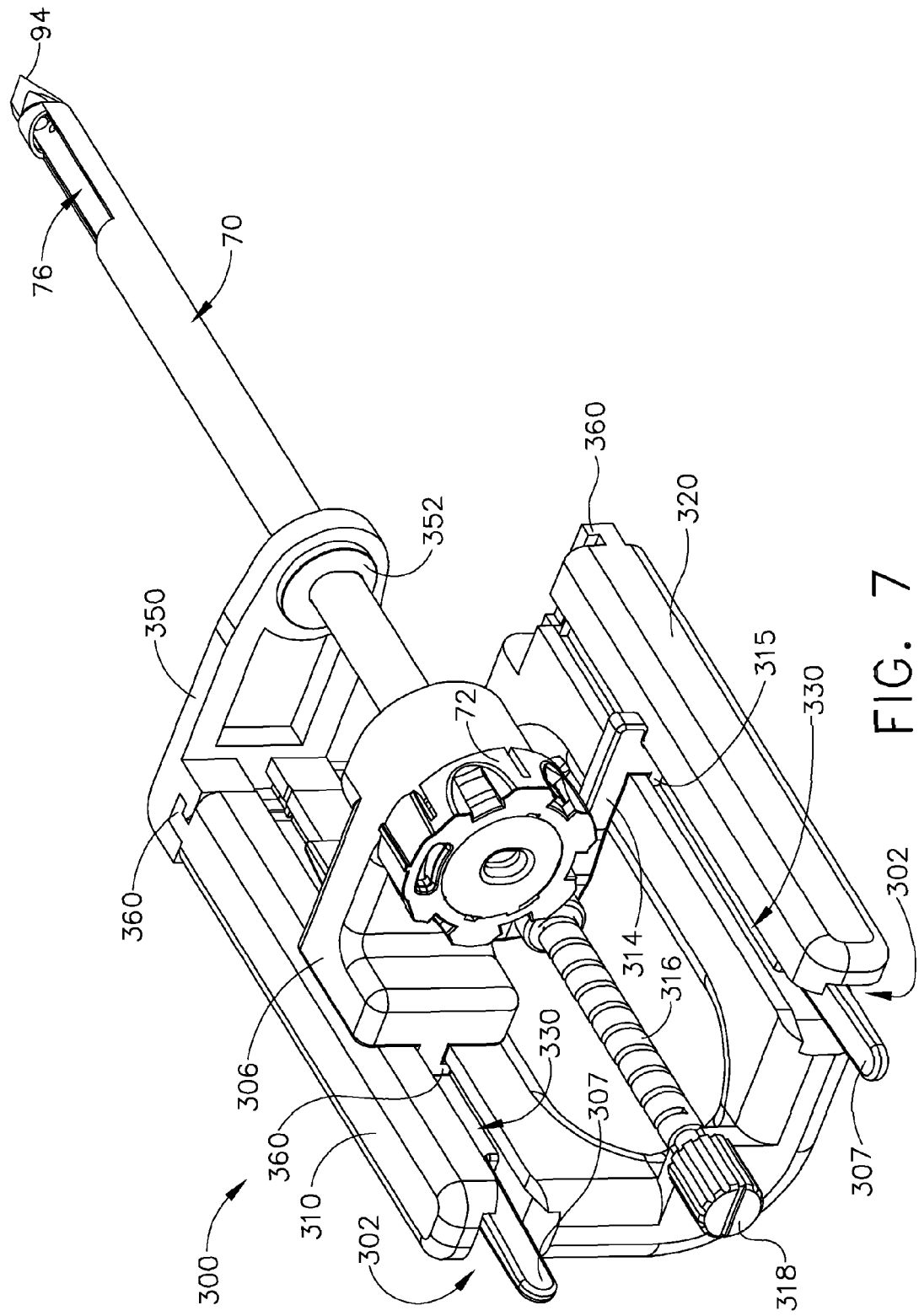
FIG. 7 depicts a perspective view of another exemplary cradle assembly for a biopsy device targeting set.
Figure 8:
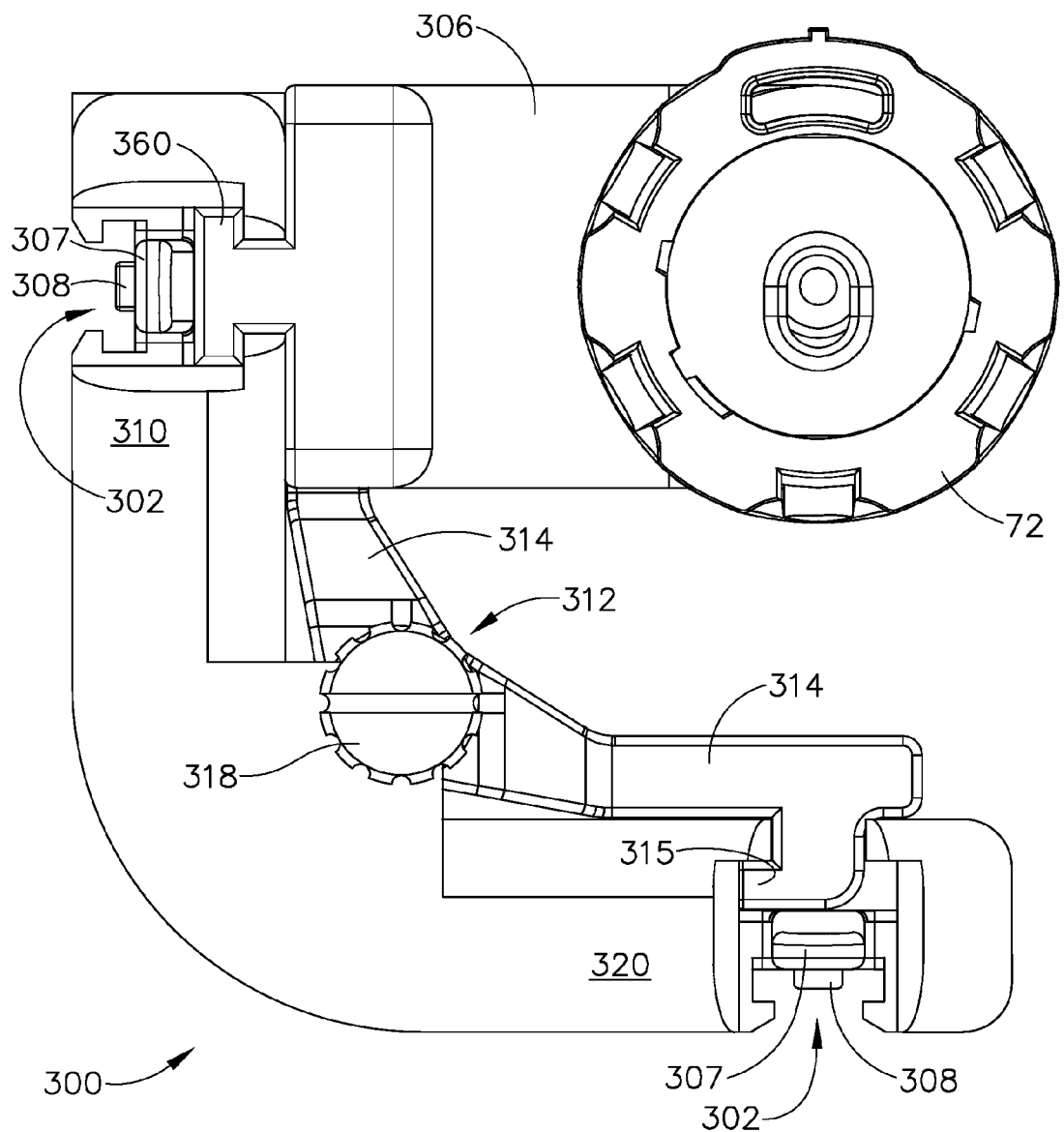
FIG. 8 depicts an end view of the cradle assembly of FIG. 7.
Figure 9:
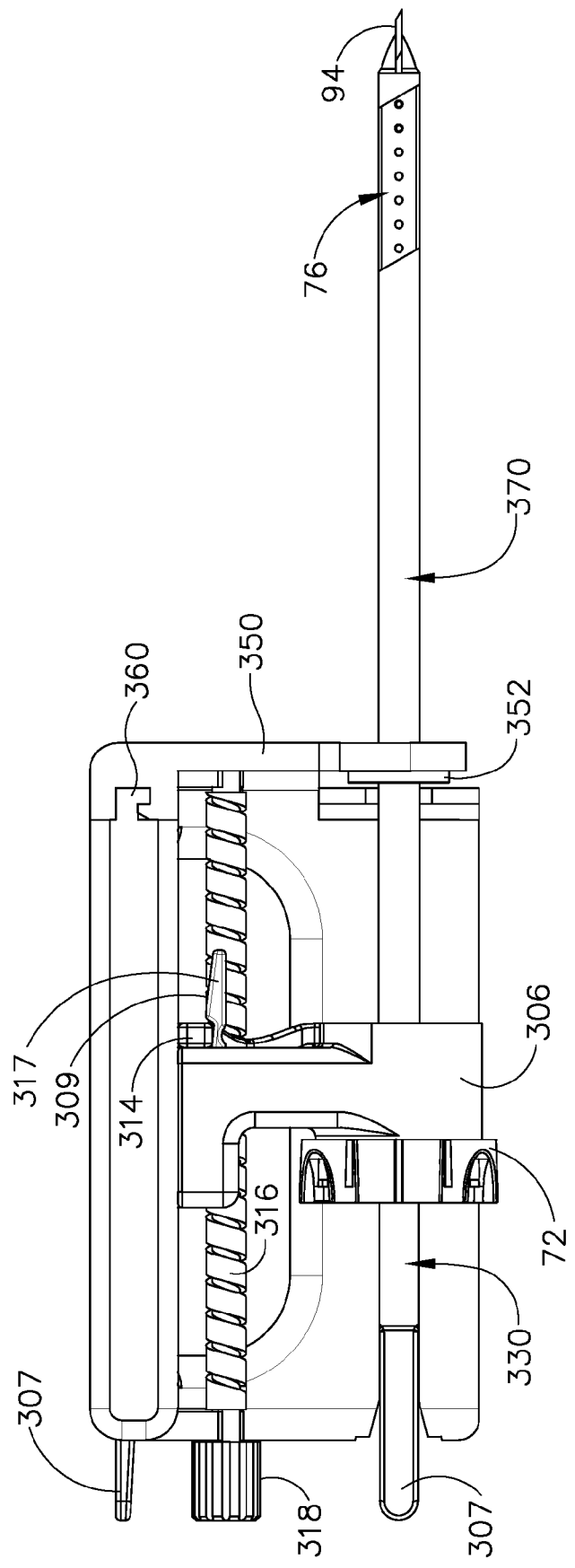
FIG. 9 depicts a top plan view of the cradle assembly of FIG. 7.
Figure 10:
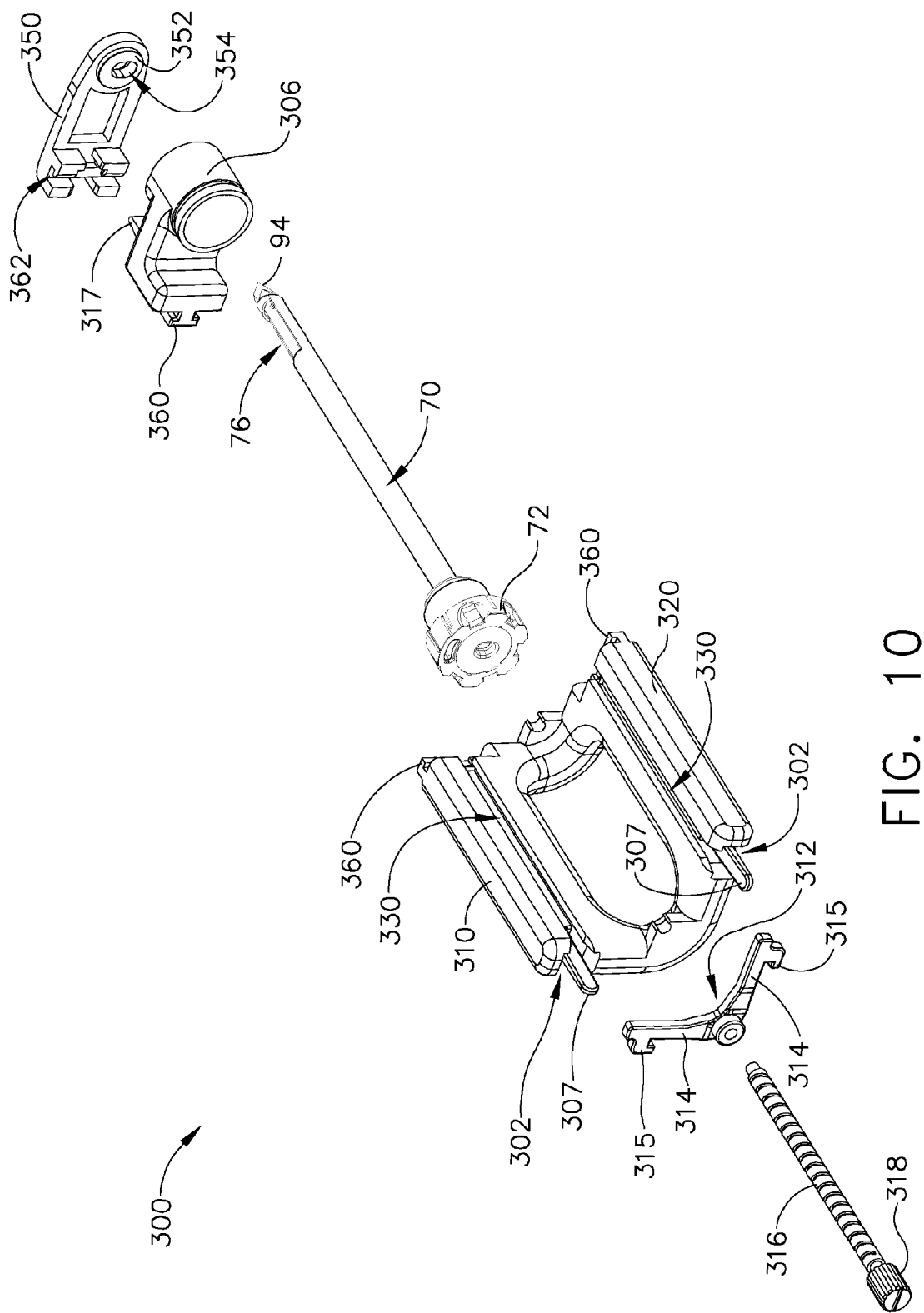
FIG. 10 depicts an exploded perspective view of the cradle assembly of FIG. 7.
Figure 11:
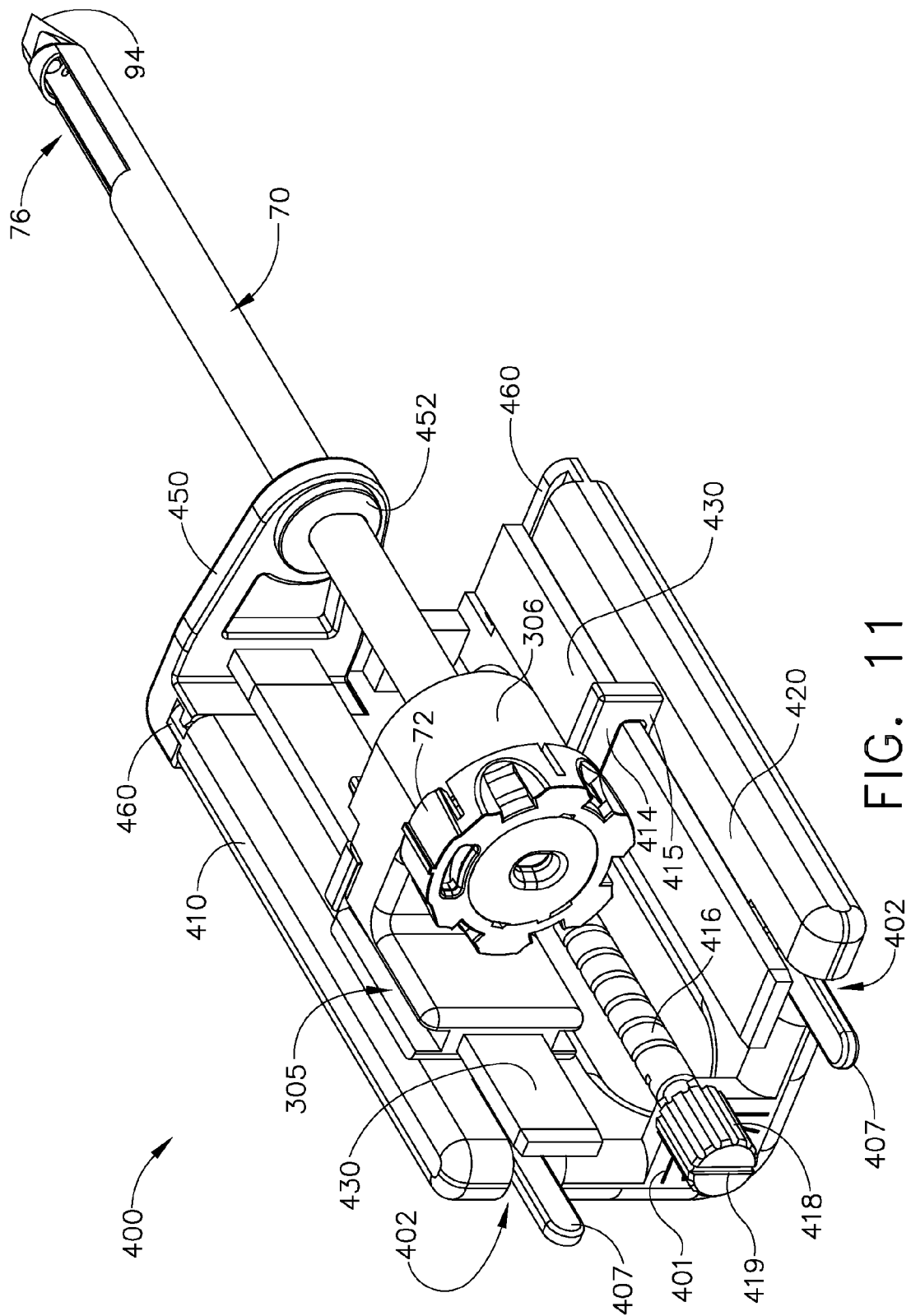
FIG. 11 depicts a perspective view of another exemplary cradle assembly for a biopsy device targeting set.

Each support arm (310, 320) also has a mounting recess (330), with which a cannula mount (306), needle mount (506), and/or biopsy device (10, 50) may be engaged. Recess (330) has a "T" shape in this example, though it should be understood that any other suitable shape may be used. Furthermore, recess (330) may be substituted or supplemented with a rail or other structure or feature, if desired. As shown in FIGS. 7-9, cannula mount (306) has a rail (360) that complements recess (330), such that rail (360) is slidingly received in recess (330) in this example. It should also be understood that a biopsy device (10, 50) may also have a rail (not shown) that complements recess (330). In such versions, sliding engagement of such a rail with recess (330) may restrict movement of a biopsy device (10, 50) relative to cradle (300); and may also provide structural support for biopsy device (10, 50). Having needle (54) of a biopsy device (10, 50) inserted in targeting cannula (70) may assist in guiding such a rail of biopsy device (10, 50) into recess (330) of cradle (300). It should be understood that such a rail of a biopsy device (10, 50) need not necessarily be engaged with the same recess (330) as cannula mount (306), though they may be engaged with the same recess (330) in some instances.

A z-stop (312) is also coupled with cradle (300) in this example. Z-stop (312) has a pair of arms (314) that are substantially perpendicular to each other. Each arm (314) has a recess engagement member (315). As shown, each recess engagement member (315) is engaged with a corresponding recess (330). Z-stop (312) is coupled with a screw gear (316), which has a rotation knob (318). It will be appreciated that an operator may manually rotate rotation knob (318) to selectively position z-stop (312) along the length of screw gear (316).

By way of example only, z-stop (312) may be used to control the depth at which a needle (30) or combined obturator (90) and targeting cannula (70) may be inserted into a patient. For instance, before coupling a cannula mount (306), needle mount (506), and/or biopsy device (10, 50) with recess (330), an operator may rotate knob (318) to set z-stop (312) at a desired longitudinal position along screw gear (316). The operator may then slide a cannula mount (306), needle mount (506), or biopsy device (10, 50) along recess (330) until a cannula mount (306), needle mount (506), or biopsy device (10, 50) engages z-stop (312), which may prevent a cannula mount (306), needle mount (506), or biopsy device (10, 50) from being advanced any further. Other mechanisms that may be used to restrict longitudinal movement of a cannula mount (306), needle mount (506), and/or biopsy device (10, 50) will be described in greater detail below, while other suitable alternatives will be apparent to those of ordinary skill in the art in view of the teachings herein.

In the present example, and as shown in FIG. 9, cannula mount (306) includes a resilient engagement tab (317), which is configured to selectively engage arm (314) of z-stop (312). Tab (317) includes a ramped underside (309), such that as cannula mount (306) is advanced toward z-stop arm (314), ramped underside (309) "rides" z-stop arm (314) to deflect tab (317) away from z-stop arm (314). When cannula mount (306) is sufficiently advanced further, tab (317) resiliently "snaps" over z-stop arm (314), providing resistance to proximal retraction of cannula mount (306) relative to z-stop arm (314). When an operator desires to remove cannula mount (306) from cradle (300), the operator may simply lift tab (317) to disengage z-stop arm (314), then pull cannula mount (306) away from z-stop arm (314). Of course, any other suitable components, features, or configurations may be used to selectively secure cannula mount (306) relative to z-stop arm (314).

A support member (350) is also secured to the distal end of cradle (300). Support member (350) includes a bushing (352), which defines an opening (354) configured to receive targeting cannula (70). Of course, a needle (30) or other structure may be inserted through opening (354). Bushing (352) is rotatable within support member (350), such that bushing (352) may be rotated to accommodate targeting cannula (70) during insertion of targeting cannula (70) through opening (354); and to rotate with targeting cannula (70) after targeting cannula (70) has been inserted through the opening. Support member (350) may provide additional support to targeting cannula (70) that is coupled with support member (350). For instance, support member (350) may reduce deflection of targeting cannula (70) when z-stop (312) (and, hence, cannula mount (306)) is positioned relatively far from support member (350). Such reduction in deflection may be particularly desirable if an operator is attempting to insert a combined obturator (90) and targeting cannula (70) along a straight line into dense tissue.

In the present example, support member (350) is rigidly secured to cradle (300). In particular, each support arm (310, 320) has a support member rail (360) extending therefrom. Support member (350) has a complementary recess (362), such that support member (350) may be slid onto either rail (360). While support member rail (360) and recess (362) have complementary "L" shapes in this example, it should be understood that any other suitable shape may be used. Furthermore, while cannula mount (306) and support member (350) are shown as being coupled with support arm (310) in this example, it should be understood that cannula mount (306) and/or support member (350) may alternatively be coupled with support arm (320). In some other versions, support member (350) is configured to selectively pivot relative to cradle (300) (e.g., to pivot it out of the way if z-stop (312) is advanced to a distal-most position). Of course, as with other components described herein, support member (350) is merely optional.

While exemplary features, components, configurations, and methods of operation for cradle (300) have been described above, it should be understood that any suitable alternatives may be used. Suitable alternative features, components, configurations, and methods of operation for cradle (300) will be apparent to those of ordinary skill in the art in view of the teachings herein.

C. Exemplary Cradle with Rail Mounting

FIGS. 11-14 depict another exemplary cradle (400), along with exemplary targeting cannula (70). Cradle (400) of this example includes unitary support arms (410, 420) that are substantially perpendicular to each other. Each support arm (410, 420) has a recess (402), which may slidingly engage a rail (108, 164) of pedestal (100), targeting grid assembly (150), or any other structure. A resilient arm (407) extends adjacent to recess (402), and includes a protrusion (408) that is configured to selectively secure cradle (400) relative to rail (108, 164). For instance, an operator may slide rail (108, 164) into either recess (402), and protrusion (408) may deflect away from rail (108, 164) then "snap" into a complementary recess (not shown) formed in rail (108, 164), such that protrusion (408) and the recess formed in rail (108, 164) restrict longitudinal motion of cradle (400) relative to rail (108, 164). To remove cradle (400) from rail (108, 164), an operator may simply lift arm (407) to disengage protrusion (408) from the recess formed in rail (108, 164), and pull cradle (400) away from rail (108, 164). Of course, any other suitable components, features, or configurations may be used to selectively secure cradle (400) relative to rail (108, 164).

Each support arm (410, 420) also has a mounting rail (430), with which a cannula mount (306), needle mount (506), and/or biopsy device (10, 50) may be engaged. Rail (430) has a "T" shape in this example, though it should be understood that any other suitable shape may be used. Furthermore, rail (430) may be substituted or supplemented with a recess or other structure or feature, if desired. As shown in FIGS. 7-9, cannula mount (306) has a recess (361) that complements rail (430), such that rail (460) is slidingly received in recess (361) in this example. It should also be understood that a biopsy device (10, 50) may also have a recess (80) that complements rail (330), as will be described in greater detail below. In such versions, sliding engagement of rail (430) with recess (80) may restrict movement of a biopsy device (10, 50) relative to cradle (300); and may also provide structural support for biopsy device (10, 50). Having needle (54) of a biopsy device (10, 50) inserted in targeting cannula (70) may assist in guiding such a rail of biopsy device (10, 50) into recess (330) of cradle (300). It should be understood that such a recess (80) of a biopsy device (10, 50) need not necessarily be engaged with the same rail (430) as cannula mount (306), though they may be engaged with the same rail (430) in some instances.

Figure 12:
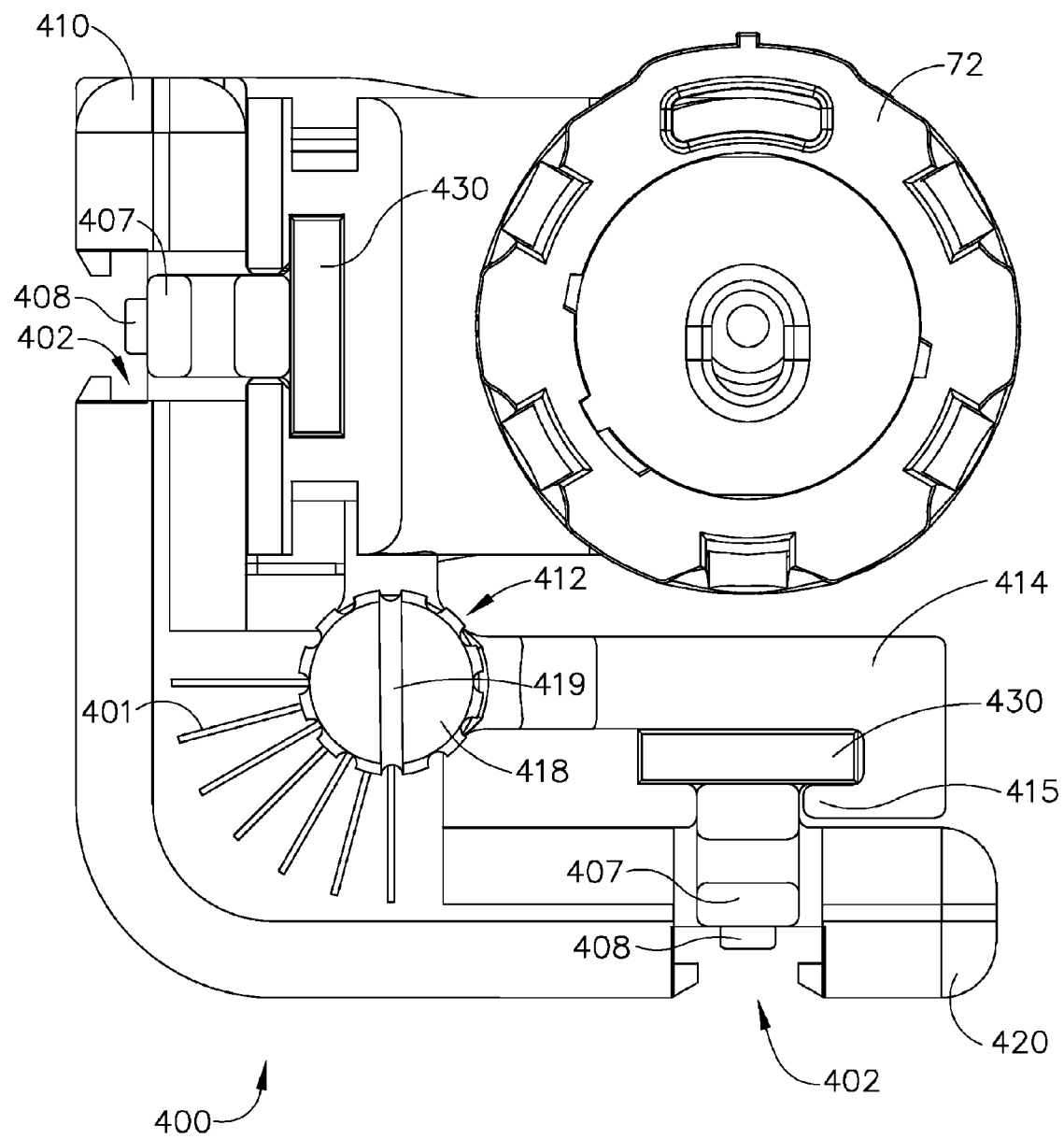
FIG. 12 depicts an end view of the cradle assembly of FIG. 11.

A z-stop (412) is also coupled with cradle (400) in this example. Z-stop (412) has a pair of arms (414) that are substantially perpendicular to each other. Each arm (414) has a rail engagement member (415). As shown, each rail engagement member (415) is engaged with a corresponding rail (430). Z-stop (412) is coupled with a screw gear (416), which has a rotation knob (418). It will be appreciated that an operator may manually rotate rotation knob (418) to selectively position z-stop (412) along the length of screw gear (416). Furthermore, as shown in FIG. 12, cradle (400) of this example includes indicia (401) configured to be read relative to a slot (419) on rotation knob (418). In particular, it will be appreciated that the relationship between slot (419) and indicia (401) may be indicative of the longitudinal position of z-stop (412) along screw gear (416). Alternatively, any other suitable features may be provided to indicate the longitudinal position of z-stop (412) along screw gear (416).

By way of example only, z-stop (412) may be used to control the depth at which a needle (30) or combined obturator (90) and targeting cannula (70) may be inserted into a patient. For instance, before coupling a cannula mount (306), needle mount (506), and/or biopsy device (10, 50) with rail (430), an operator may rotate knob (418) to set z-stop (412) at a desired longitudinal position along screw gear (416). The operator may then slide a cannula mount (306), needle mount (506), or biopsy device (10, 50) along rail (430) until a cannula mount (306), needle mount (506), or biopsy device (10, 50) engages z-stop (412), which may prevent a cannula mount (306), needle mount (506), or biopsy device (10, 50) from being advanced any further. Other mechanisms that may be used to restrict longitudinal movement of a cannula mount (306), needle mount (506), and/or biopsy device (10, 50) will be described in greater detail below, while other suitable alternatives will be apparent to those of ordinary skill in the art in view of the teachings herein.

Figure 13:
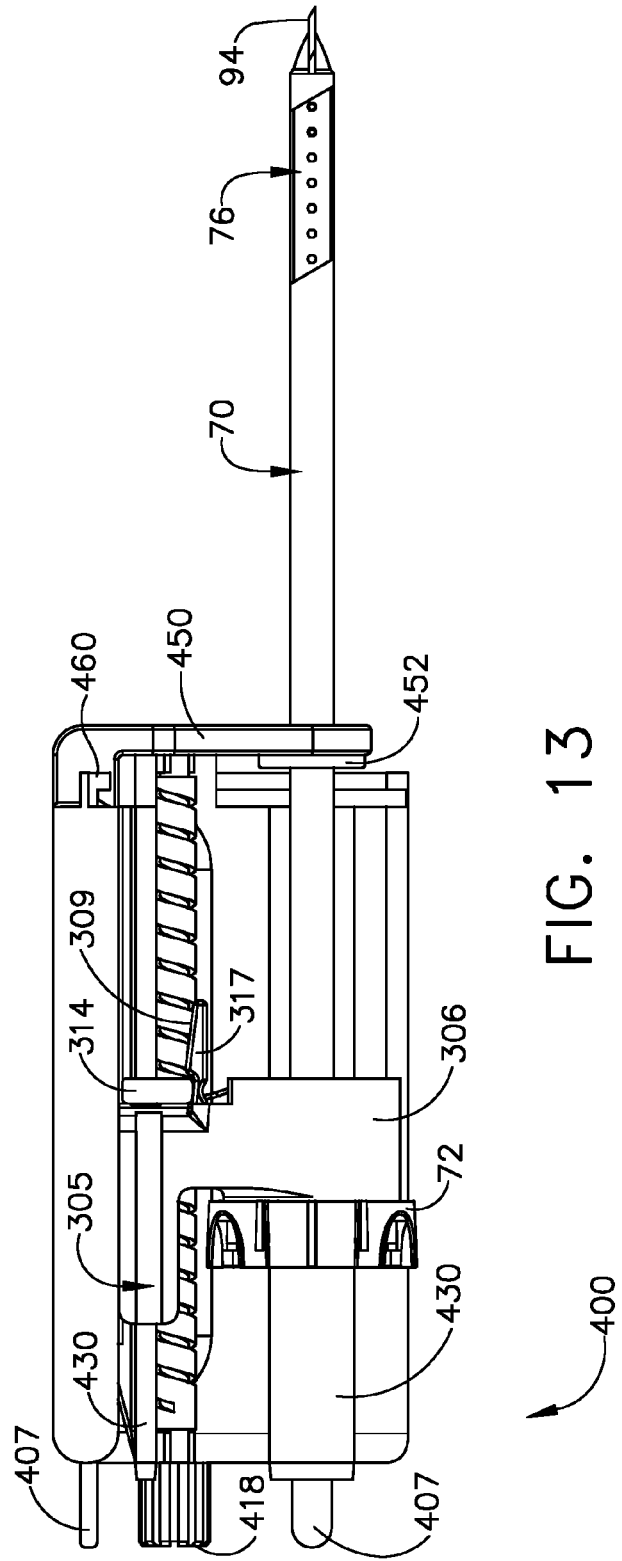
FIG. 13 depicts a top plan view of the cradle assembly of FIG. 11.
Figure 14:
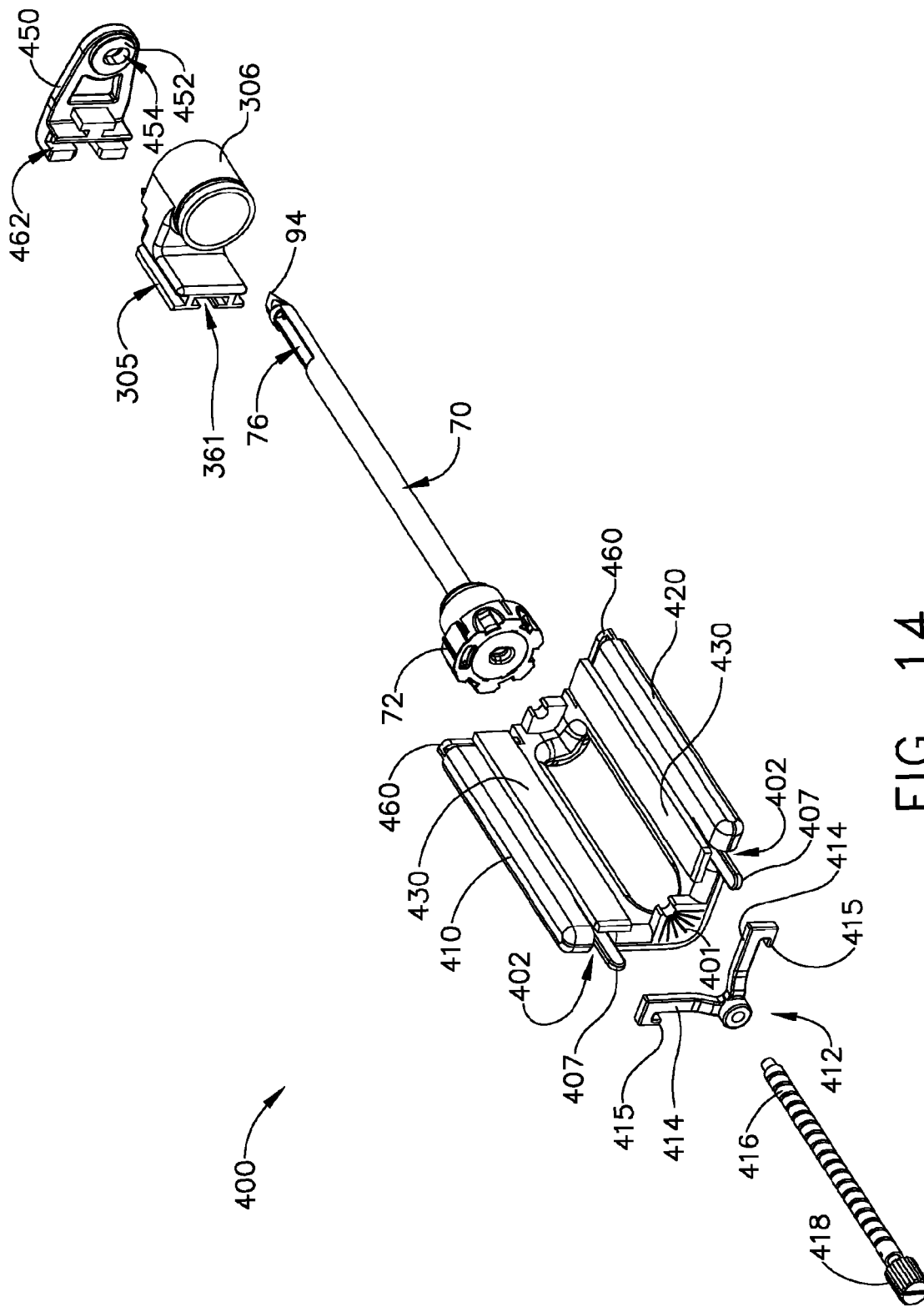
FIG. 14 depicts an exploded perspective view of the cradle assembly of FIG. 11.
Figure 15:
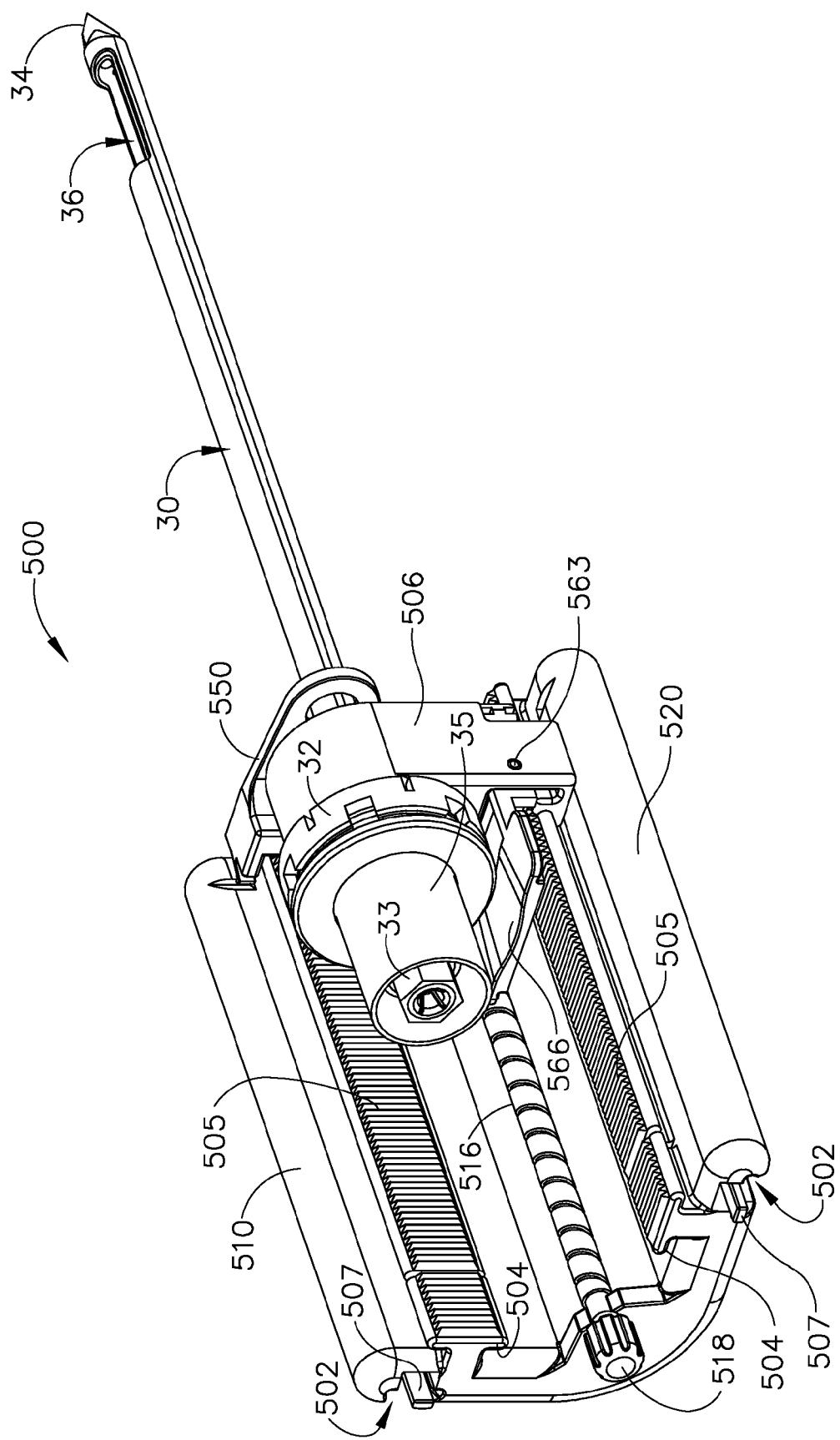
FIG. 15 depicts a perspective view of another exemplary cradle assembly for a biopsy device targeting set.

In the present example, and as shown in FIG. 13, cannula mount (306) includes a resilient engagement tab (317), which is configured to selectively engage arm (414) of z-stop (412). Tab (317) is configured to operate with arm (414) in the same manner as described above with respect to arm (312). Of course, any other suitable components, features, or configurations may be used to selectively secure cannula mount (306) relative to z-stop arm (414).

A support member (450) is also secured to the distal end of cradle (400). Support member (450) includes a bushing (452), which defines an opening (454) configured to receive targeting cannula (70). Of course, a needle (30) or other structure may be inserted through opening (454). Bushing (452) is rotatable within support member (450), such that bushing (452) may be rotated to accommodate targeting cannula (70) during insertion of targeting cannula (70) through opening (454); and to rotate with targeting cannula (70) after targeting cannula (70) has been inserted through the opening. Support member (450) may provide additional support to targeting cannula (70) that is coupled with support member (450). For instance, support member (450) may reduce deflection of targeting cannula (70) when z-stop (412) (and, hence, cannula mount (306)) is positioned relatively far from support member (450). Such reduction in deflection may be particularly desirable if an operator is attempting to insert a combined obturator (90) and targeting cannula (70) along a straight line into dense tissue.

In the present example, support member (450) is rigidly secured to cradle (400). In particular, each support arm (410, 420) has a support member rail (460) extending therefrom. Support member (450) has a complementary recess (462), such that support member (450) may be slid onto either rail (460). While support member rail (460) and recess (462) have complementary "L" shapes in this example, it should be understood that any other suitable shape may be used. Furthermore, while cannula mount (306) and support member (450) are shown as being coupled with support arm (410) in this example, it should be understood that cannula mount (306) and/or support member (450) may alternatively be coupled with support arm (420). In some other versions, support member (450) is configured to selectively pivot relative to cradle (400) (e.g., to pivot it out of the way if z-stop (412) is advanced to a distal-most position). Of course, as with other components described herein, support member (450) is merely optional.

While exemplary features, components, configurations, and methods of operation for cradle (400) have been described above, it should be understood that any suitable alternatives may be used. Suitable alternative features, components, configurations, and methods of operation for cradle (400) will be apparent to those of ordinary skill in the art in view of the teachings herein.

III. Exemplary Ratcheting Cannula Mount

While several examples of cradles (500, 600, 700) will be discussed below in the context of either a detachable needle (30) or a targeting cannula (70), it should be understood that cradles (500, 600, 700) may also be used with the other of a detachable needle (30) or a targeting cannula (70). Furthermore, it should be understood that any of the below described cradles (500, 600, 700) may be subject to any desired addition, omission, variation, modification, substitution, supplementation, or method of use.

A. Exemplary Cannula Mount with Lower Release Button

FIGS. 15-18 depict another exemplary cradle (500), which has a detachable needle (30) coupled therewith. Cradle (500) of this example includes unitary support arms (510, 520) that are substantially perpendicular to each other. Each support arm (510, 520) has a recess (502), which may slidingly engage a rail (108, 164) of pedestal (100), targeting grid assembly (150), or any other structure. A resilient arm (507) extends adjacent to recess (502), and includes a protrusion (508) that is configured to selectively secure cradle (500) relative to rail (108, 164). For instance, an operator may slide rail (108, 164) into either recess (502), and protrusion (508) may deflect away from rail (108, 164) then "snap" into a complementary recess (not shown) formed in rail (108, 164), such that protrusion (508) and the recess formed in rail (108, 164) restrict longitudinal motion of cradle (500) relative to rail (108, 164). To remove cradle (500) from rail (108, 164), an operator may simply lift arm (507) to disengage protrusion (508) from the recess formed in rail (108, 164), and pull cradle (500) away from rail (108, 164). Of course, any other suitable components, features, or configurations may be used to selectively secure cradle (500) relative to rail (108, 164).

Figure 16:
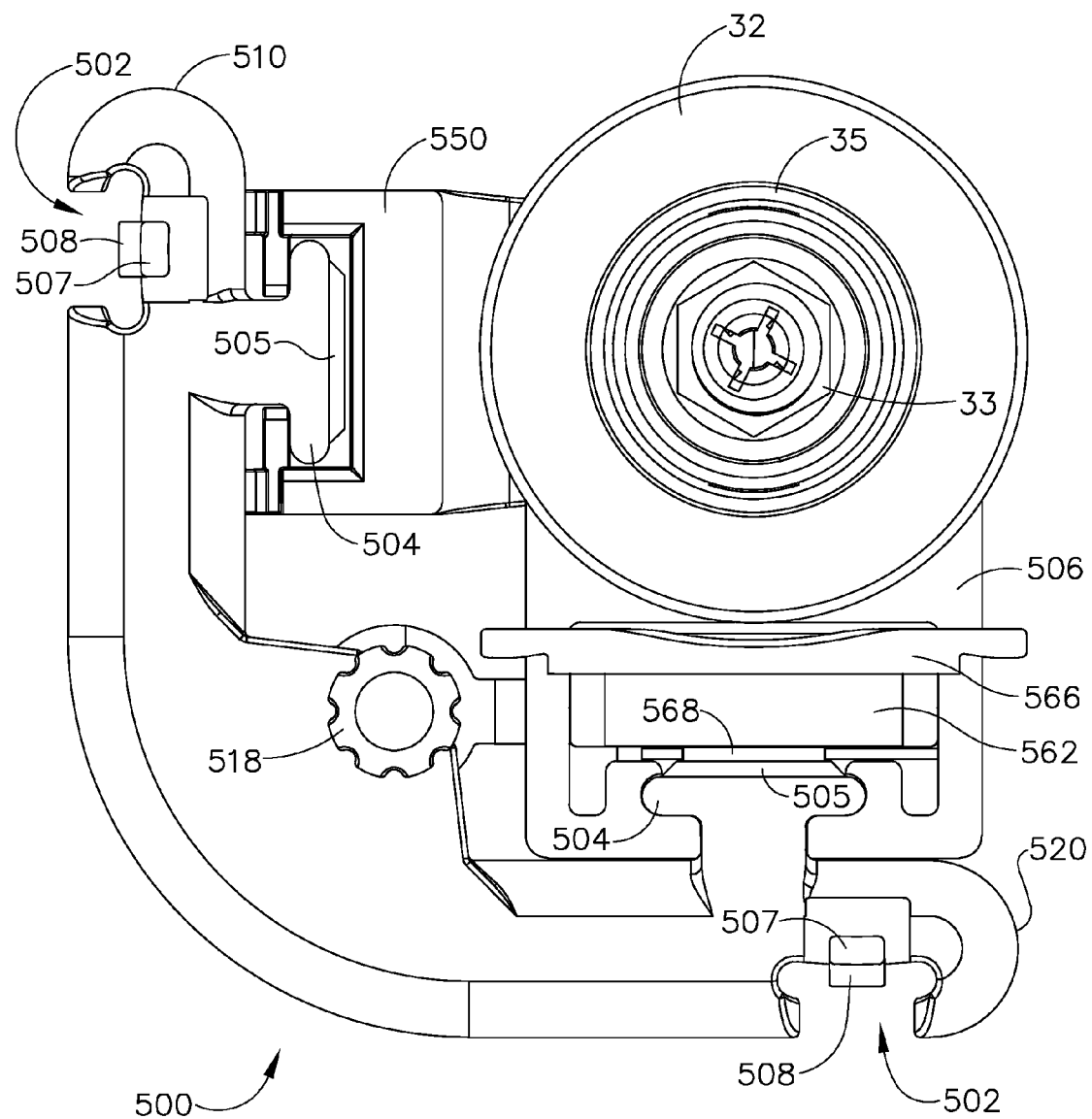
FIG. 16 depicts an end view of the cradle assembly of FIG. 15.
Figure 17:
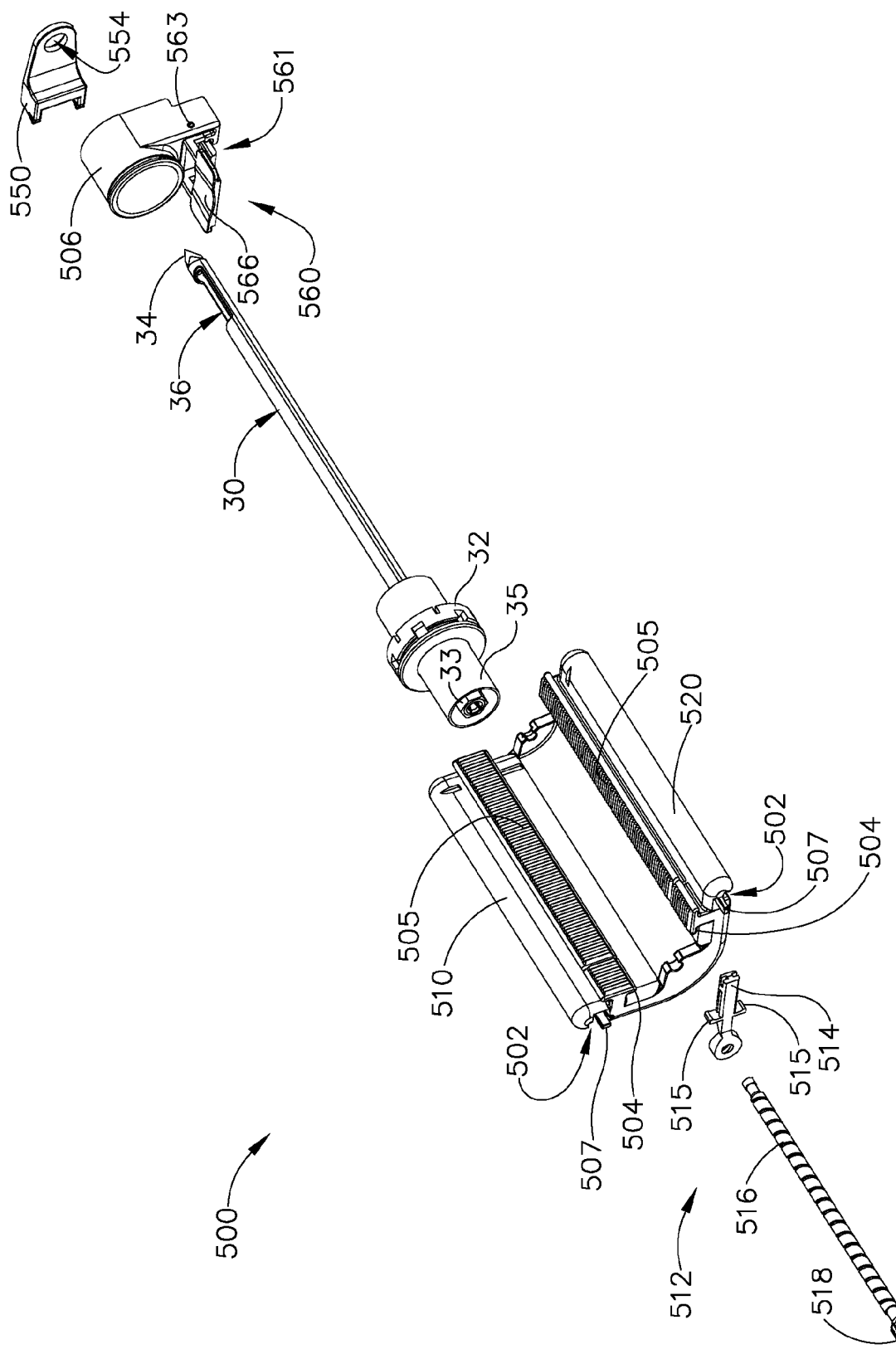
FIG. 17 depicts an exploded perspective view of the cradle assembly of FIG. 15.
Figure 18:
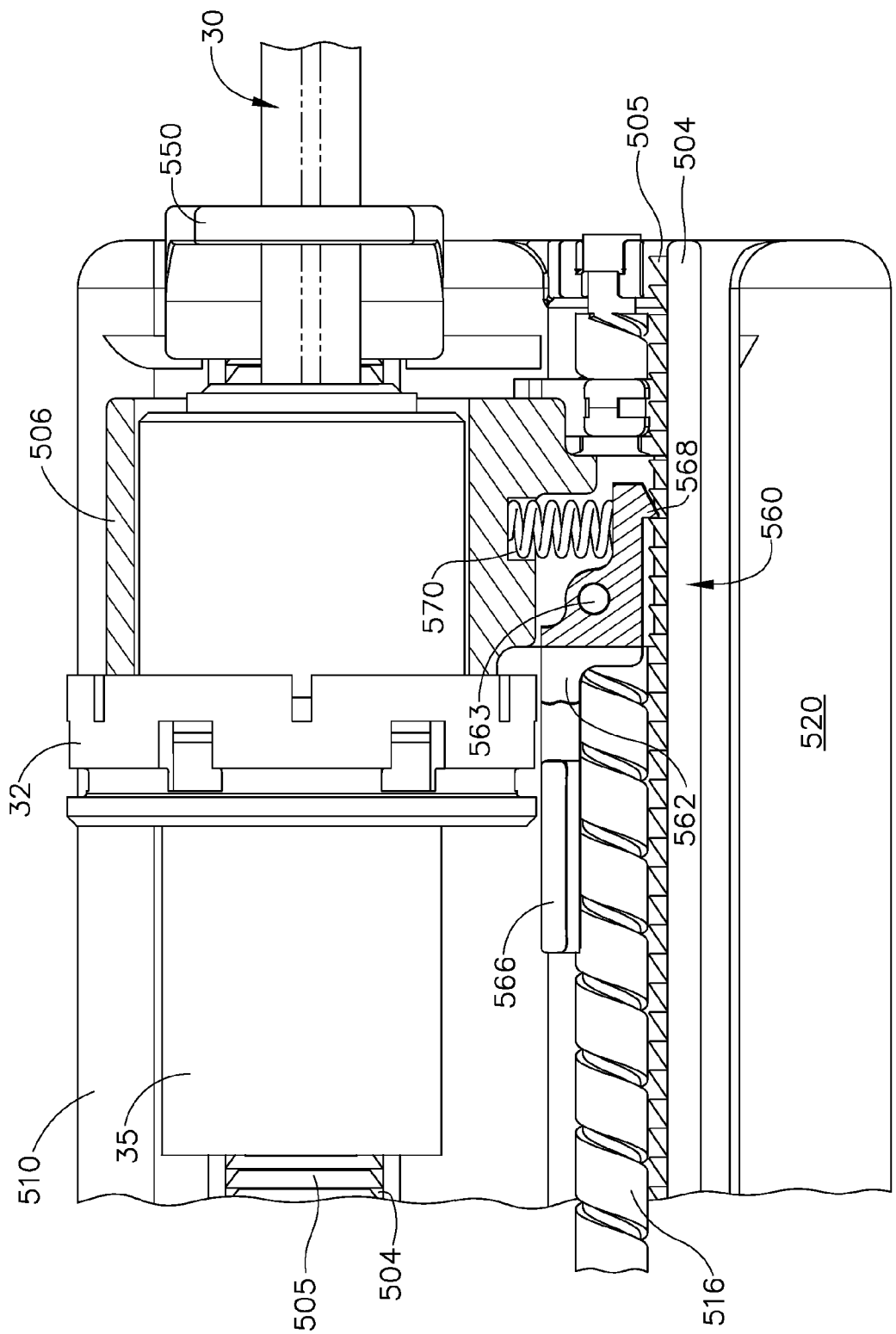
FIG. 18 depicts a partial cross-sectional side view of the cradle assembly of FIG. 15, showing a ratcheting mechanism.

Each support arm (510, 520) also has a mounting rail (504), with which a cannula mount (306), needle mount (506), and/or biopsy device (10, 50) may be engaged. Rail (504) has a "T" shape in this example, though it should be understood that any other suitable shape may be used. Furthermore, rail (504) may be substituted or supplemented with a recess or other structure or feature, if desired. As shown in FIGS. 16-17, needle mount (506) has a recess (561) that complements rail (504), such that rail (504) is slidingly received in recess (561) in this example. It should also be understood that a biopsy device (10, 50) may also have a recess (80) that complements rail (504), as will be described in greater detail below. In such versions, sliding engagement of rail (504) with recess (80) may restrict movement of a biopsy device (10, 50) relative to cradle (500); and may also provide structural support for biopsy device (10, 50). Rail (504) may also guide a needle-less biopsy device (10) into engagement with thumbwheel (32), drive member (33), and sleeve (35) of detachable needle (30). Examples of such engagement, as well as additional details and variations of such components, are described in U.S. Non-Provisional patent application Ser. No. 12/337,674, entitled "BIOPSY DEVICE WITH SLIDING CUTTER COVER," filed on even date herewith, the disclosure of which is incorporated by reference herein. However, it should be understood that a recess (80) of a biopsy device (10) need not necessarily be engaged with the same rail (504) as needle mount (506), though they may be engaged with the same rail (504) in some instances.

A z-stop (512) is also coupled with cradle (500) in this example. Z-stop (512) has an arm (514) that has a pair of opposing rail engagement members (515). Z-stop (512) is coupled with a screw gear (516), which has a rotation knob (518). It will be appreciated that an operator may manually rotate rotation knob (518) to selectively position z-stop (512) along the length of screw gear (516). By way of example only, z-stop (512) may be used to control the depth at which a needle (30) or combined obturator (90) and targeting cannula (70) may be inserted into a patient. For instance, before coupling a cannula mount (306), needle mount (506), and/or biopsy device (10, 50) with rail (504), an operator may rotate knob (418) to set z-stop (412) at a desired longitudinal position along screw gear (416). The operator may then slide a cannula mount (306), needle mount (506), or biopsy device (10, 50) along rail (504) until a cannula mount (306), needle mount (506), or biopsy device (10, 50) engages z-stop (512), which may prevent a cannula mount (306), needle mount (506), or biopsy device (10, 50) from being advanced any further. Other mechanisms that may be used to restrict longitudinal movement of a cannula mount (306), needle mount (506), and/or biopsy device (10, 50) will be described in greater detail below, while other suitable alternatives will be apparent to those of ordinary skill in the art in view of the teachings herein. It should also be understood that z-stop (512) may be disengaged from one rail (504) and then be engaged with another rail (504), in a manner similar to z-stop (212) as discussed above.

A support member (550) is also secured to the distal end of cradle (500). Support member (550) defines an opening (554) configured to receive needle (30). Of course, a targeting cannula (70) or other structure may be inserted through opening (554). Support member (550) may provide additional support to needle (30) that is coupled with support member (550). For instance, support member (550) may reduce deflection of needle (30) when z-stop (512) (and, hence, needle mount (506)) is positioned relatively far from support member (550). Such reduction in deflection may be particularly desirable if an operator is attempting to insert needle (30) along a straight line into dense tissue. Support member (550) is shown as being removably coupled with support arm (510) in FIG. 15. However, it should be understood that support member (550) may be removed by an operator and coupled with support arm (520) instead. Such removable coupling may be provided through a snap fit or any other suitable type of fit. Of course, as with other components described herein, support member (550) is merely optional.

Needle mount (506) of the present example has a ratcheting mechanism (560), which is operable to selectively secure the longitudinal position of needle mount (506) along rail (504). Ratcheting mechanism (560) comprises an arm (562), which is pivotally secured to needle mount (506) by a pivot pin (563). Arm (562) includes a push-tab (566) at one end and a pawl (568) at the other end. Push-tab (566) is presented proximally behind needle mount (506), such that a user may depress push-tab (566) to rotate arm (562) about pivot pin (563). Pawl (568) is configured to selectively engage teeth (505) of rail (504). In particular, pawl (568) is configured to "ride" over teeth (505) as needle mount (506) is advanced distally along rail (504) (e.g., until needle mount (506) engages z-stop (512)); while restricting proximal longitudinal motion of needle mount (506) along rail (504). A spring (570) is positioned above pawl (568), and is biased to urge pawl (568) into engagement with teeth (505). Of course, ratcheting mechanism (560) may have any other suitable components, features, configurations, or methods of operation.

In a merely exemplary use, an operator is provided with a needle (30), which is coupled with a needle mount (506), but which is separate from a cradle (500). The operator rotates knob (518) to translate z-stop (512) along screw gear (516), thereby setting a depth of insertion for needle (30). The operator then slides needle mount (506) onto rail (504), while guiding tip (34) of needle (30) through opening (554) of support member (550). The operator continues to translate needle mount (506) along rail (504) until needle mount (506) engages z-stop (512). As needle mount (506) is translated along rail (504), pawl (568) rides over teeth (505) under the bias of spring (570). The operator then couples a biopsy device (10) with needle (30) and obtains a desired number of tissue samples. When the operator needs to move needle mount (506) proximally along rail (504), such as to provide a shallower depth of insertion or to remove needle mount (506) from cradle (500), the operator depresses push-tab (556) to disengage pawl (568) from teeth (505). Arm (562) pivots about pivot pin (563) and spring (570) compresses as operator holds down push-tab (556). While holding push-tab (556) down, the operator may then pull needle mount (506) proximally along rail (504), if not pull needle mount (506) completely off of cradle (500).

While exemplary features, components, configurations, and methods of operation for cradle (500) have been described above, it should be understood that any suitable alternatives may be used. Suitable alternative features, components, configurations, and methods of operation for cradle (500) will be apparent to those of ordinary skill in the art in view of the teachings herein.

B. Exemplary Cannula Mount with Upper Release Button

Figure 19:
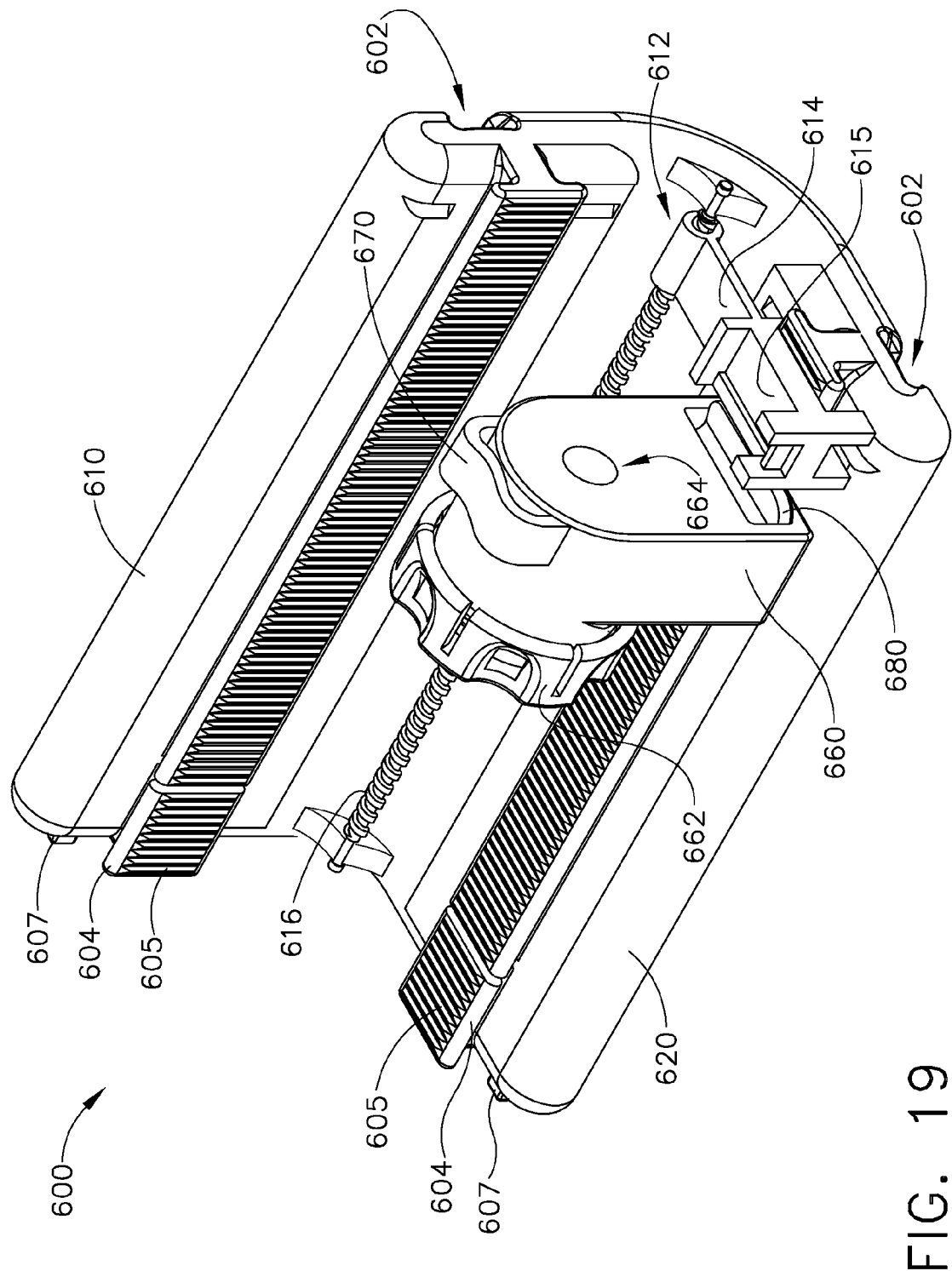
FIG. 19 depicts a perspective view of another exemplary cradle assembly for a biopsy device targeting set.
Figure 20:
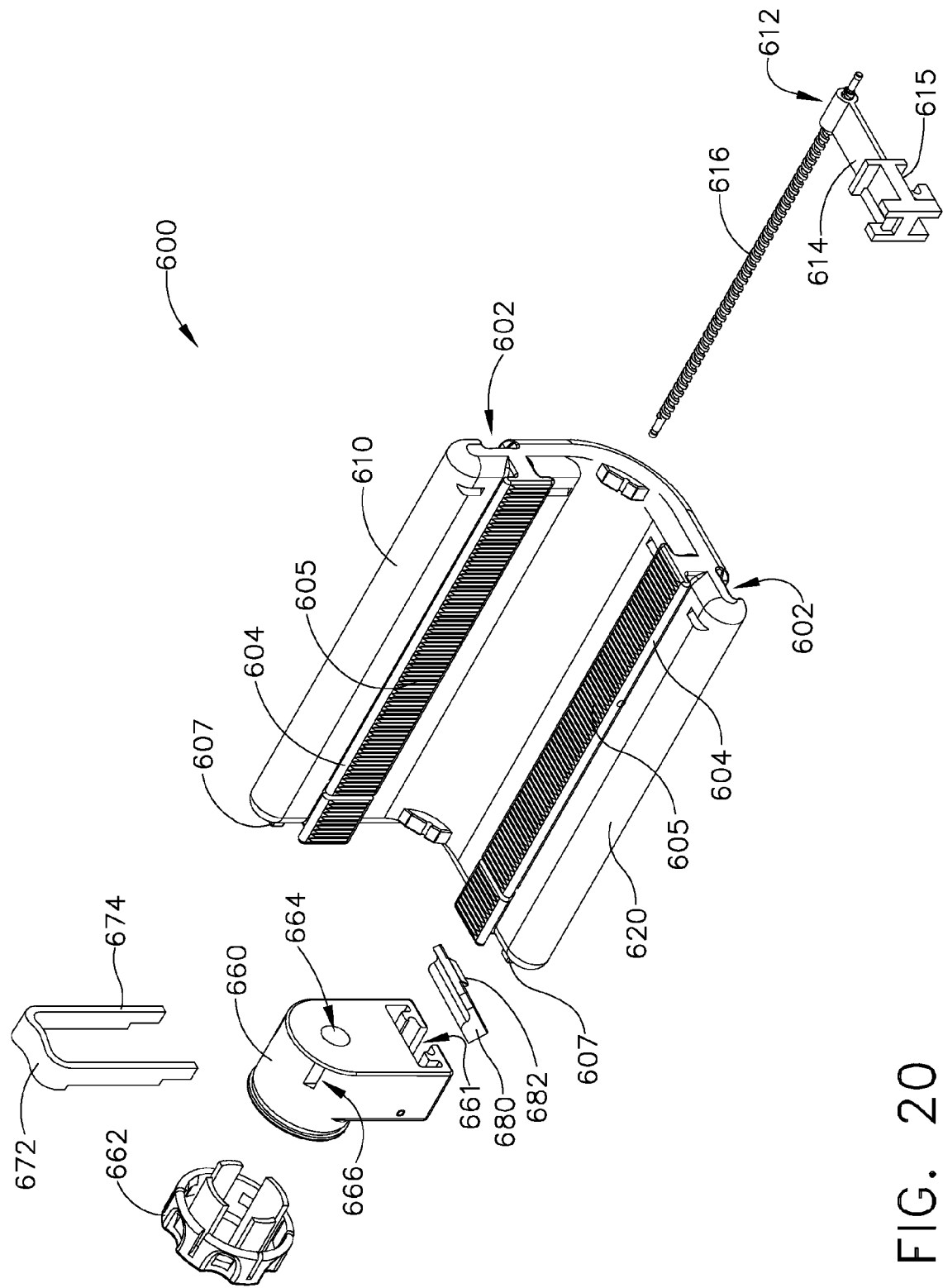
FIG. 20 depicts an exploded perspective view of the cradle assembly of FIG. 19.
Figure 21:
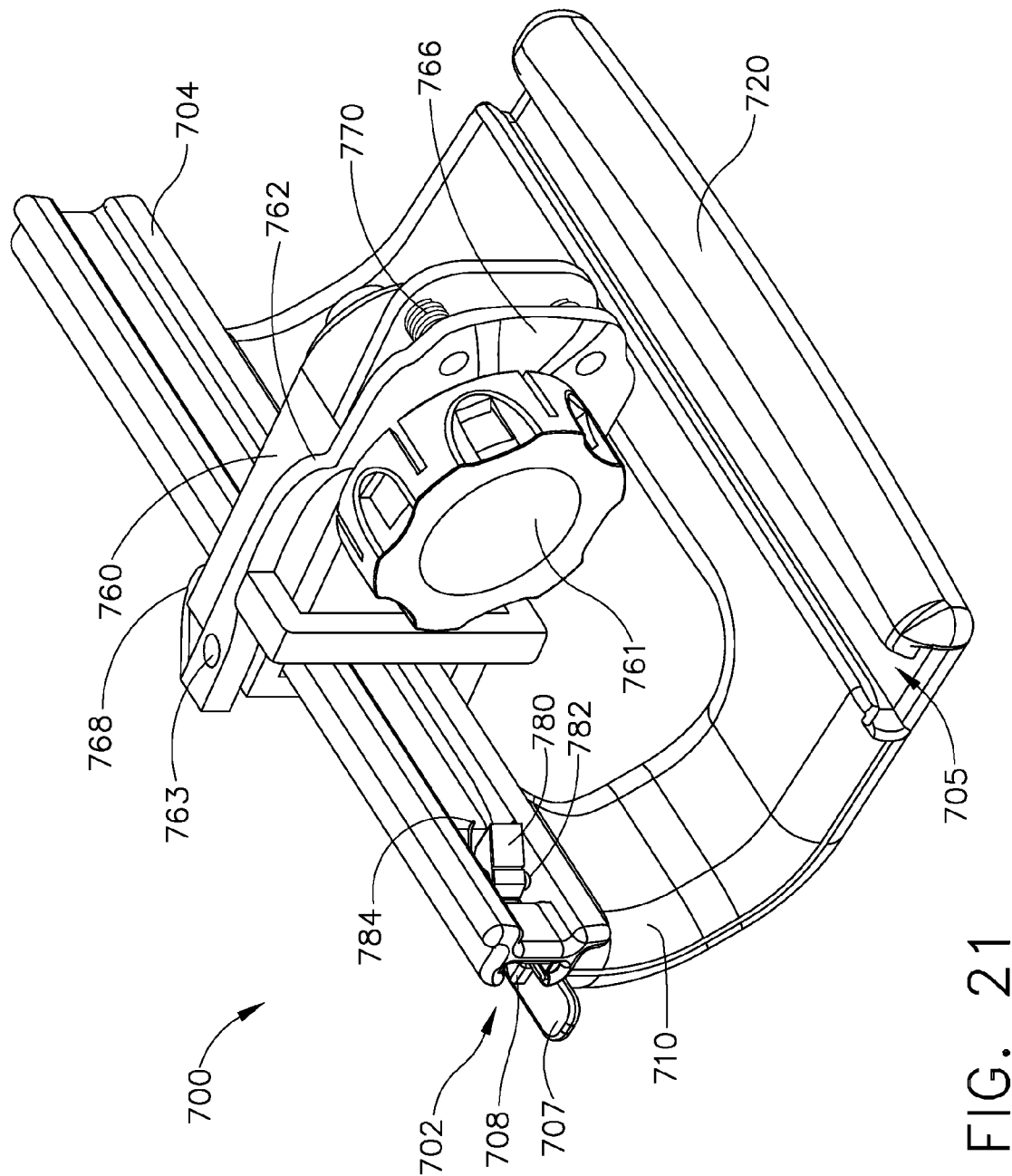
FIG. 21 depicts a perspective view of another exemplary cradle assembly for a biopsy device targeting set.

FIGS. 19-20 depict yet another exemplary cradle (600), which includes a ratcheting mount (660) coupled therewith. Cradle (600) of this example includes unitary support arms (610, 620) that are substantially perpendicular to each other. Each support arm (610, 620) has a recess (602), which may slidingly engage a rail (108, 164) of pedestal (100), targeting grid assembly (150), or any other structure. A resilient arm (607) extends adjacent to recess (602), and includes a protrusion (not shown) that is configured to selectively secure cradle (600) relative to rail (108, 164). Cradle (600) may thus be selectively coupled with or decoupled from a rail (108, 164) in a manner similar to other cradles (300, 400, 500) described above. Of course, any other suitable components, features, or configurations may be used to selectively secure cradle (600) relative to rail (108, 164).

Each support arm (610, 620) also has a mounting rail (604), with which a cannula mount (306), needle mount (506), and/or biopsy device (10, 50) may be engaged. Rail (604) has a "T" shape in this example, though it should be understood that any other suitable shape may be used. Furthermore, rail (604) may be substituted or supplemented with a recess or other structure or feature, if desired. As shown in FIG. 20, ratcheting mount (660) has a recess (661) that complements rail (604), such that rail (604) is slidingly received in recess (661) in this example. It should also be understood that a biopsy device (10, 50) may also have a recess (80) that complements rail (604), as will be described in greater detail below. In such versions, sliding engagement of rail (604) with recess (80) may restrict movement of a biopsy device (10, 50) relative to cradle (600); and may also provide structural support for biopsy device (10, 50). However, it should be understood that a recess (80) of a biopsy device (10, 50) need not necessarily be engaged with the same rail (604) as ratcheting mount (660), though they may be engaged with the same rail (604) in some instances.

A z-stop (612) is also coupled with cradle (600) in this example. Z-stop (612) has an arm (614) that has a rail engagement member (615). Z-stop (612) is coupled with a screw gear (616), which may be coupled with a rotation knob (not shown). It will be appreciated that an operator may manually rotate such a rotation knob to selectively position z-stop (612) along the length of screw gear (616). Z-stop (612) may thus be operated in a manner similar to other z-stops (212, 312, 412, 512) as described above. For instance, an operator may slide ratcheting mount (660) along rail (604) until ratcheting mount (660) engages z-stop (612), which may prevent a ratcheting mount (660) from being advanced any further. Other mechanisms that may be used to restrict longitudinal movement of a ratcheting mount (660), cannula mount (306), needle mount (506), and/or biopsy device (10, 50) will be described in greater detail below, while other suitable alternatives will be apparent to those of ordinary skill in the art in view of the teachings herein. It should also be understood that z-stop (612) may be disengaged from one rail (604) and then be engaged with another rail (604), in a manner similar to z-stop (212) as discussed above.

A support member (not shown) may also be secured to the distal end of cradle (600), if desired. Such a support member may have components, features, and methods of operation similar to support members (220, 350, 450, 550) described above.

Ratcheting mount (660) of the present example includes a thumbwheel (662), a push-member (670), and a ratcheting lever (680). A needle (30), targeting cannula (70), or any other device may be coupled with ratcheting mount (660). For instance, a needle (30) or targeting cannula (70) may protrude distally through opening (664) formed in ratcheting mount (660), and may couple with thumbwheel (662) in any suitable fashion (e.g., removable coupling, as described herein, etc.). Ratcheting lever (680) of this example includes a pawl (682), which is configured to selectively engage teeth (605) of rail (604). In particular, pawl (682) is configured to "ride" over teeth (605) as ratcheting mount (660) is advanced distally along rail (604) (e.g., until ratcheting mount (660) engages z-stop (612)); while restricting proximal longitudinal motion of ratcheting mount (660) along rail (604). A spring (not shown) is positioned above pawl (682), and is biased to urge pawl (682) into engagement with teeth (605).

A pair of upright members (674) extend downwardly from push-member (670) in this example. In particular, upright members (674) are received through slots (666) formed in ratcheting mount (660), and engage a first end of ratcheting lever (680). This first end is opposite to the end of ratcheting lever (680) presenting pawl (682). A pivot pin (not shown) is inserted through ratcheting lever (680), between these two ends. Ratcheting lever (680) may thus operate similar to arm (562), as described above. In will also be understood that push-member (670) may operate similar to push-tab (556) described above.

In a merely exemplary use, an operator is provided with a ratcheting mount (660), which is separate from a cradle (600). The operator rotates screw gear (616) to translate z-stop (612) along screw gear (616), thereby setting a depth of insertion for a needle (30) or targeting cannula (70) that will be coupled with ratcheting mount (660). The operator then slides ratcheting mount (660) onto rail (604), and continues to translate ratcheting mount (660) along rail (604) until ratcheting mount (660) engages z-stop (612). As ratcheting mount (660) is translated along rail (604), pawl (682) rides over teeth (605) under the bias of a spring (not shown). The operator then couples a biopsy device (10, 50) and a needle (30) or targeting cannula (70) with ratcheting mount (660) and with cradle (600), and obtains a desired number of tissue samples. When the operator needs to move ratcheting mount (660) proximally along rail (604), such as to provide a shallower depth of insertion or to remove ratcheting mount (660) from cradle (600), the operator depresses push-member (670) to disengage pawl (682) from teeth (605). Ratcheting lever (680) pivots about a pivot pin (not shown) and a spring (not shown) compresses as operator holds down push-member (670). While holding push-member (670) down, the operator may then pull ratcheting mount (660) proximally along rail (604), if not pull ratcheting mount (660) completely off of cradle (600).

While exemplary features, components, configurations, and methods of operation for cradle (600) have been described above, it should be understood that any suitable alternatives may be used. Suitable alternative features, components, configurations, and methods of operation for cradle (600) will be apparent to those of ordinary skill in the art in view of the teachings herein.

C. Exemplary Cannula Mount with Side Release Button

FIGS. 21-24 depict yet another exemplary cradle (700), which includes another exemplary ratcheting mount (760) coupled therewith. Cradle (700) of this example includes unitary support arms (710, 720) that are substantially perpendicular to each other. Support arm (710) has a recess (702), which may slidingly engage a rail (108, 164) of pedestal (100), targeting grid assembly (150), or any other structure. A resilient arm (707) extends adjacent to recess (702), and includes a protrusion (708) that is configured to selectively secure cradle (700) relative to rail (108, 164). Cradle (700) may thus be selectively coupled with or decoupled from a rail (108, 164) in a manner similar cradle (200) described above. Of course, any other suitable components, features, or configurations may be used to selectively secure cradle (700) relative to rail (108, 164).

Figure 22:
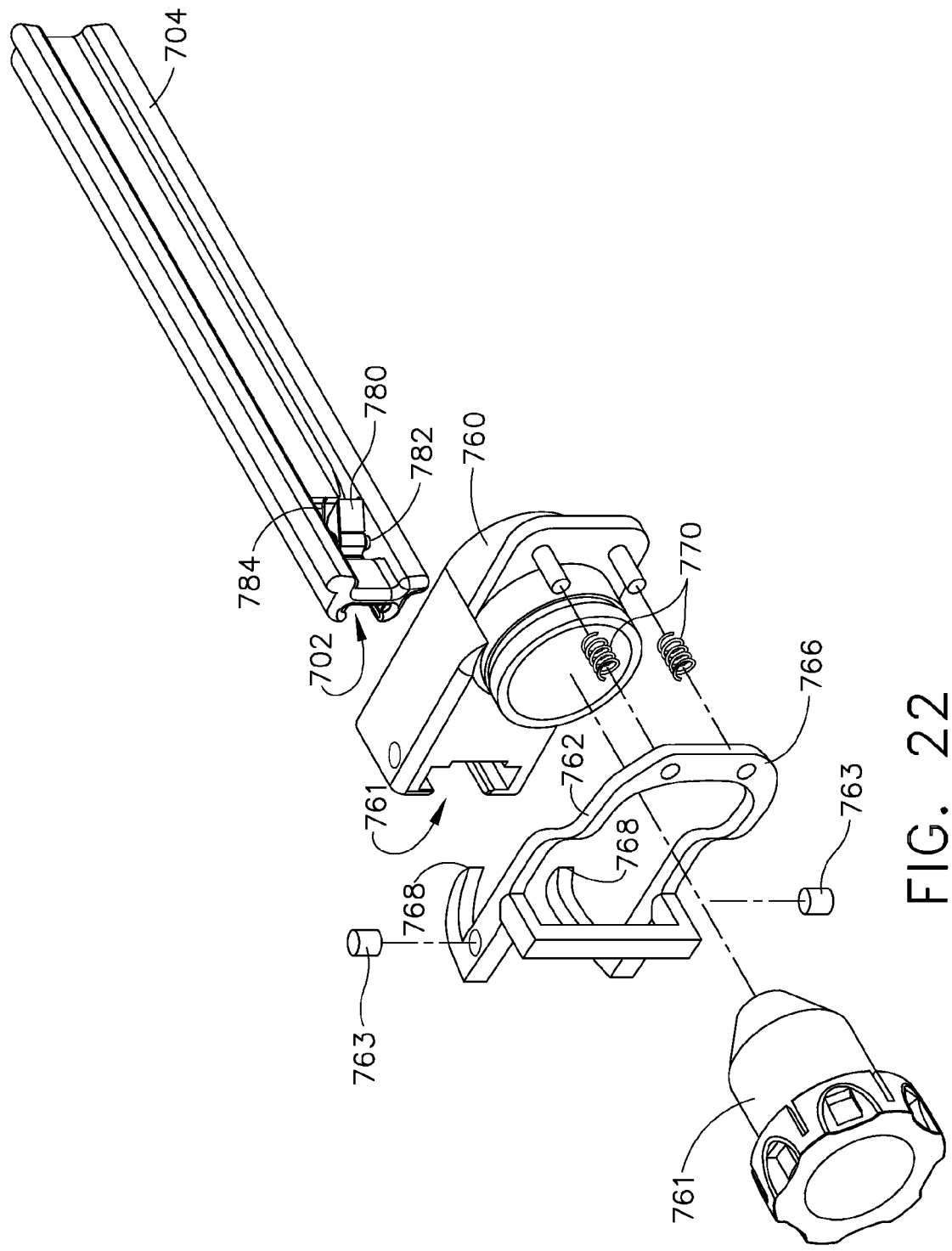
FIG. 22 is an exploded view of a pawl and ratcheting z-stop assembly of the cradle assembly of FIG. 21.

Support arm (710) has a mounting rail (704), while support arm (720) has a mounting recess (705). A cannula mount (306), needle mount (506), and/or biopsy device (10, 50) may be engaged with either or both of mounting rail (704) or mounting recess (705). Mounting rail (704) and mounting recess (705) each have a "T" shape in this example, though it should be understood that any other suitable shape may be used. Furthermore, mounting rail (704) and/or mounting recess (705) may be substituted or supplemented with a recess or other structure or feature, if desired. As shown in FIG. 22, ratcheting mount (760) has a recess (761) that complements rail (704), such that rail (704) is slidingly received in recess (761) in this example. It should also be understood that a biopsy device (10, 50) may also have a recess (80) that complements mounting rail (704); and/or a rail that complements mounting recess (705). In such versions, sliding engagement of mounting rail (704) with recess (80), or sliding reengagement of a recess with mounting rail (705), may restrict movement of a biopsy device (10, 50) relative to cradle (700); and may also provide structural support for biopsy device (10, 50). However, it should be understood that a recess (80) of a biopsy device (10, 50) need not necessarily be engaged with the same mounting rail (704) as ratcheting mount (760) (e.g., biopsy device (10, 50) may instead be engaged with mounting recess (705)), though they may both be engaged with the same mounting rail (704) in some instances.

Figure 23:
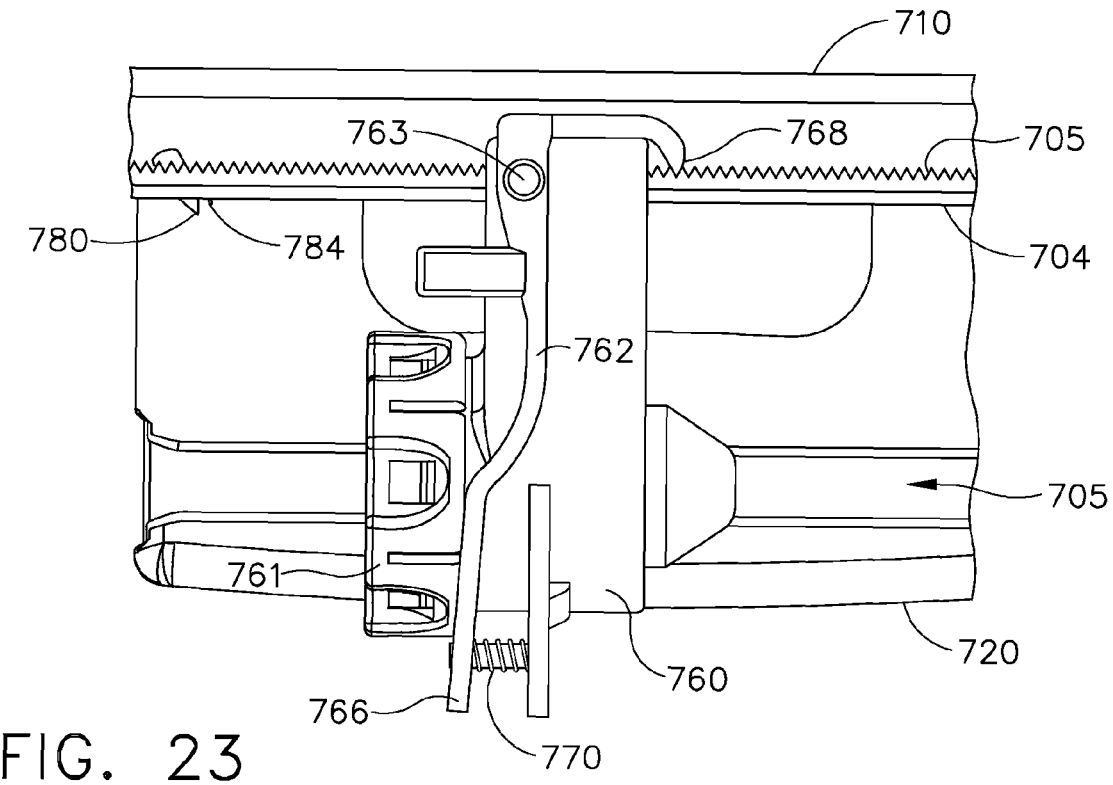
FIG. 23 is a top view of the cradle assembly of FIG. 21, showing the ratcheting z-stop assembly in a locked configuration.
Figure 24:
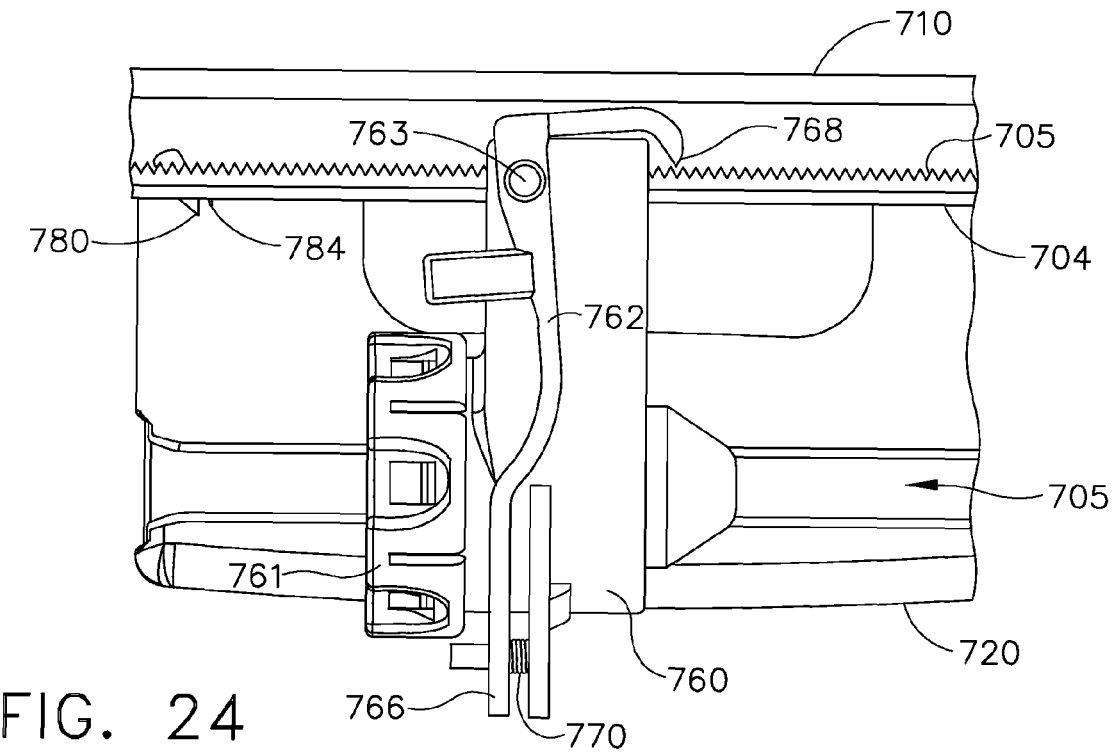
FIG. 24 is a top view of the cradle assembly of FIG. 21, showing the ratcheting z-stop assembly in an unlocked configuration.

As shown in FIGS. 23-24, rail (704) includes a plurality of teeth (705) along its backside. Teeth (705) are configured to engage pawls (768) as will be described in greater detail below. Rail (704) also includes a locking pawl (780), which is configured to restrict proximal movement of ratcheting mount (760) along rail (704). In particular, locking pawl (780) is pivotally mounted on a pin (782), about which locking pawl (780) may rotate. A torsion spring (784) is positioned about pin (782), and is engaged with locking pawl (780) and with rail (704). Torsion spring (784) is configured to bias locking pawl (780) outwardly relative to rail (704). It will be appreciated in view of FIGS. 23-24 that the configuration and orientation of locking pawl (780) may permit ratcheting mount (760) to be advanced distally onto rail (704) while preventing ratcheting mount (760) from being pulled proximally off of rail (704). In particular, locking pawl (780) may pivot out of the way as ratcheting mount (760) is advanced onto rail (704) and past locking pawl (780). After ratcheting mount (760) has "cleared" locking pawl (780), spring (784) may move locking pawl (780) back to its outwardly oriented position. In order to pull ratcheting mount (760) back proximally off of rail (704) an operator may manually push locking pawl (780) back out of the way to permit ratcheting mount (760) to clear locking pawl (780). It should be understood that a variety of other features, components, or configurations may be used to restrict proximal movement of ratcheting mount (760), in addition to or in lieu of locking pawl (780). It should also be understood that any other cradle (200, 300, 400, 500, 600) described herein may include a locking pawl (780) or a similar feature. Of course, a locking pawl (780) may be omitted altogether, if desired.

While not shown, it should be understood that cradle (700) may also be provided with a z-stop. It should also be understood that ratcheting mount (760) may itself serve as a z-stop by restricting distal movement of a biopsy device (10, 50) or other component that is coupled with cradle (700). Similarly, a support member (not shown) may also be secured to the distal end of cradle (700), if desired. Such a support member may have components, features, and methods of operation similar to support members (220, 350, 450, 550) described above.

Ratcheting mount (760) of the present example includes a thumbwheel (761) and an arm (762), which is pivotally secured to ratcheting mount (760) by a pair of pivot pins (763). Arm (762) includes a push-tab (766) at one end and a pair of pawls (768) at the other end. Push-tab (766) is presented lateral to ratcheting mount (760), such that a user may depress push-tab (766) to rotate arm (762) about pivot pins (763). Pawls (768) are configured to selectively engage teeth (705) of rail (704). In particular, pawls (768) are configured to "ride" over teeth (705) as ratcheting mount (760) is advanced distally along rail (704); while restricting proximal longitudinal motion of ratcheting mount (760) along rail (704). Springs (770) are between push-tab (766), and are biased to urge pawls (768) into engagement with teeth (705). Of course, ratcheting mount (760) may have any other suitable components, features, configurations, or methods of operation.

In a merely exemplary use, an operator is provided with a ratcheting mount (760), which is separate from a cradle (700). The operator slides ratcheting mount (760) onto rail (704), and continues to translate ratcheting mount (760) along rail (704) until reaching a desired longitudinal position along rail (704). As ratcheting mount (760) is translated along rail (704), pawls (782) ride over teeth (705) under the bias of springs (770). The operator then couples a biopsy device (10, 50) and a needle (30) or targeting cannula (70) with ratcheting mount (760) and with cradle (700), and obtains a desired number of tissue samples. When the operator needs to move ratcheting mount (760) proximally along rail (704), such as to provide a shallower depth of insertion or to remove ratcheting mount (760) from cradle (700), the operator depresses push-tab (766) to disengage pawls (782) from teeth (705) (FIG. 24). Arm (762) pivots about pivot pins (763) and springs (770) compress as operator holds down push-tab (766). While holding push-tab (766) down, the operator may then pull ratcheting mount (760) proximally along rail (704). To the extent that the operator wishes to remove ratcheting mount (760) from cradle (700), the operator may also depress locking pawl (780), to provide sufficient clearance to allow ratcheting mount (760) to pass over locking pawl (780) as ratcheting mount (760) is pulled proximally off of rail (704).

While exemplary features, components, configurations, and methods of operation for cradle (700) have been described above, it should be understood that any suitable alternatives may be used. Suitable alternative features, components, configurations, and methods of operation for cradle (600) will be apparent to those of ordinary skill in the art in view of the teachings herein.

IV. Exemplary Coupling of Biopsy Probe with Cradle and Mount

Figure 25:
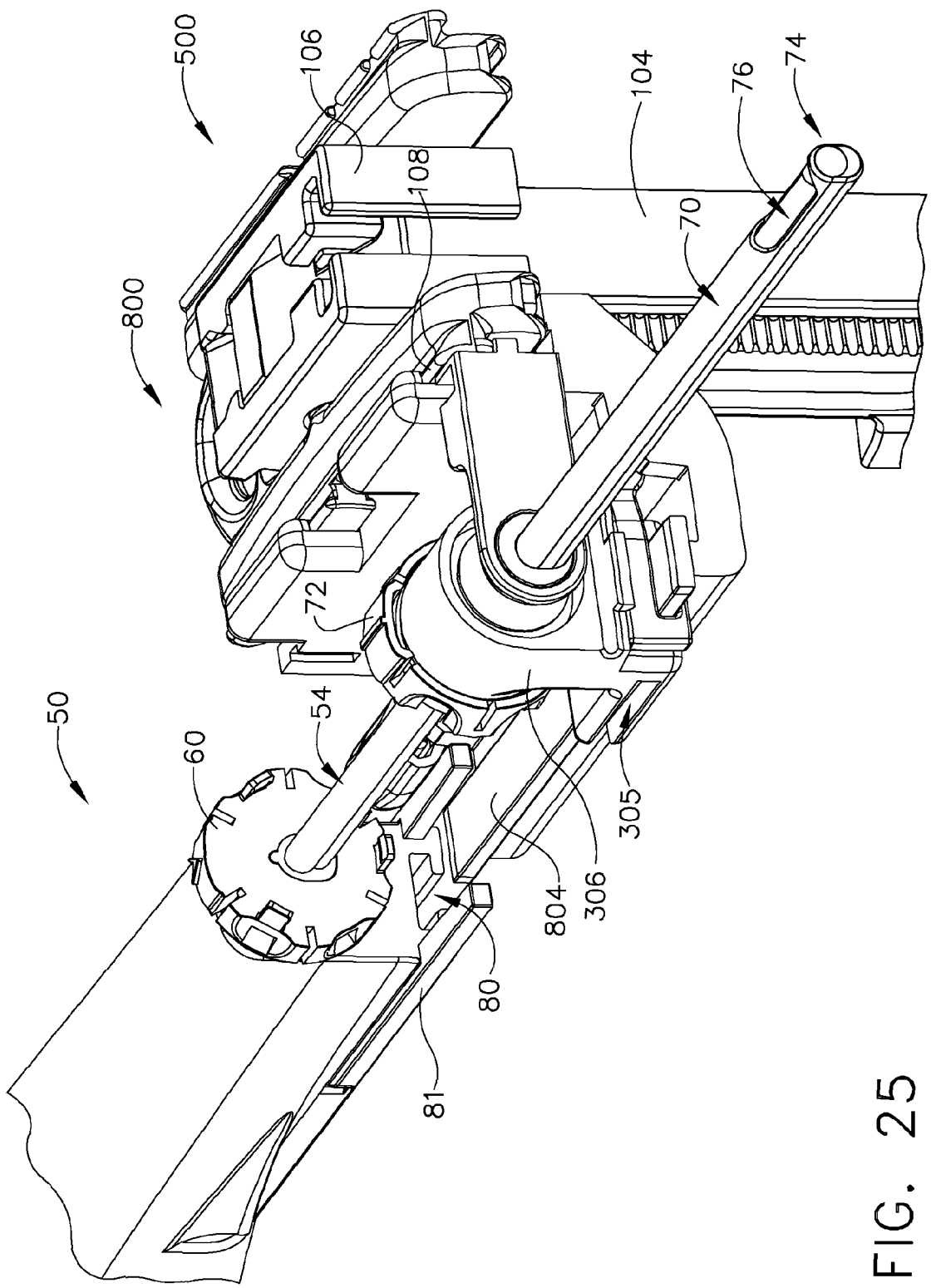
FIG. 25 shows a partial perspective view of an exemplary biopsy probe in a preliminary stage of engagement with an exemplary targeting set.
Figure 26:
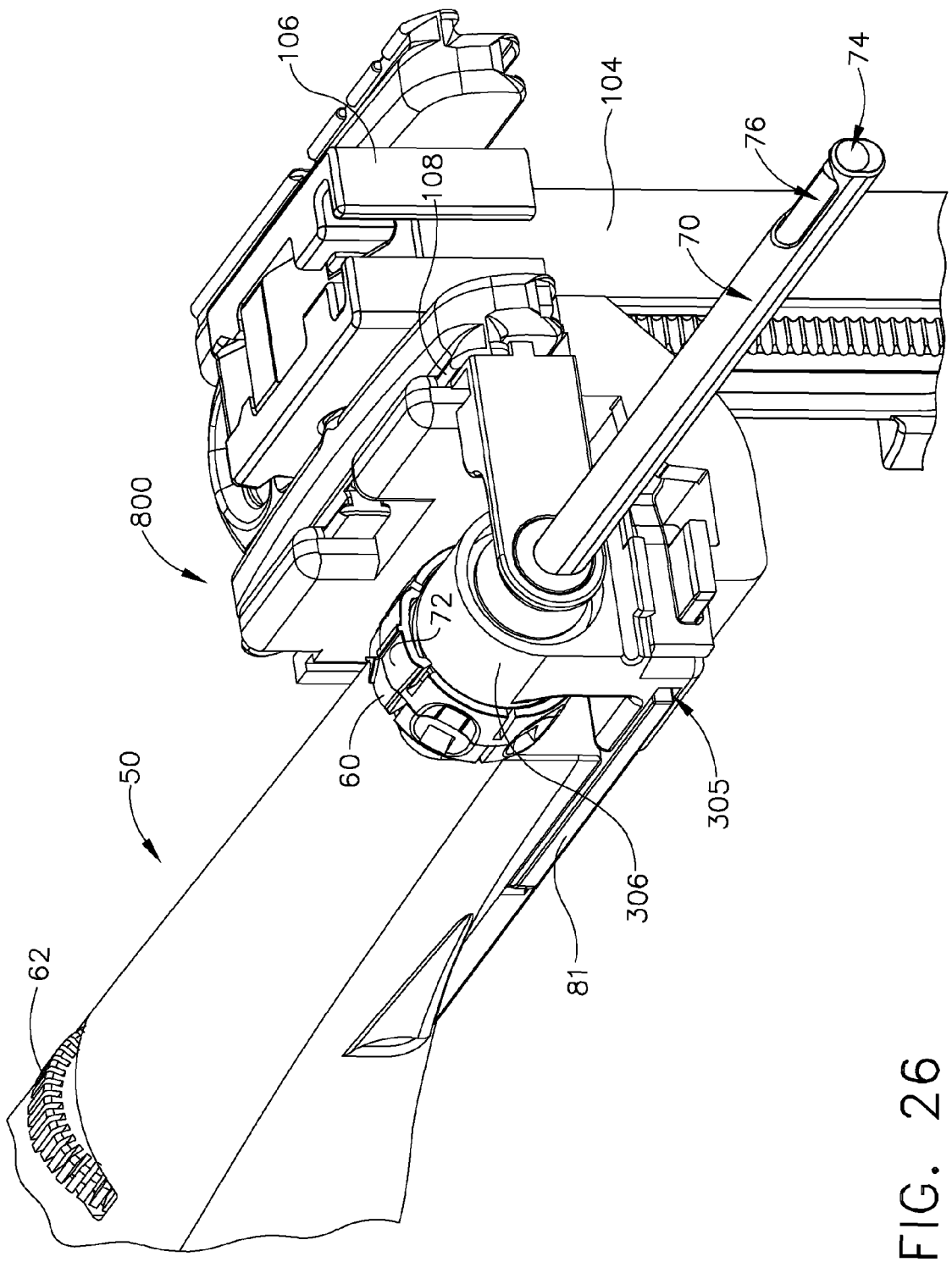
FIG. 26 shows a partial perspective view of the biopsy probe and targeting set of FIG. 25, in a subsequent stage of engagement.

FIGS. 25-26 and FIGS. 27-28 each depict a series showing a biopsy device (50, 75) engaging a cradle (800) and a cannula mount (306) in an exemplary fashion. For instance, in FIGS. 25-26, a biopsy probe (50) has a mounting recess (80) and a pair of unitary distally extending mounting arms (81). As also shown in FIGS. 25-26, cradle (800) has a rail (804) that complements recess (80); while cannula mount (306) has a pair of recesses (305) that complement mounting arms (81). In particular, as biopsy device (50) is advanced distally, rail (804) enters recess (80);

while arms (81) enter recesses (305). Biopsy device (50) continues to be advanced until thumbwheel (60) couples with thumbwheel (72). Biopsy device (50) is then supported by cradle (800) and pedestal (500).

It will be appreciated that having various areas of engagement may provide substantial support and rigid stabilization for biopsy device (50). In particular, biopsy device (50) may be supported and/or stabilized at least in part by engagement between the following components: needle (54) with cannula (70), thumbwheel (60) with thumbwheel (72), recess (80) with rail (804), and mounting arms (81) with recesses (305). It should also be understood that engagement may be provided in several stages as biopsy device (50) is advanced toward cannula mount (306). For instance, in the present example, needle (54) engages cannula (70) first. Then recess (80) engages rail (804) as biopsy device is advanced further. Then mounting arms (81) engage recesses (305) as biopsy device (50) is advanced further still. Finally, thumbwheel (60) engages thumbwheel (72) as advancement of biopsy device (50) is completed. Substantial support and stabilization for biopsy device (50) may be particularly desirable to the extent that all support for biopsy device (50) is being provided at the distal end of biopsy device (50) in this example, and further considering that the center of mass of biopsy device may be a substantial distance proximal to the distal end of biopsy device (50). Such a distal positioning of the center of mass may create substantial stresses at support regions at the distal end of biopsy device (50). Of course, biopsy device (50) may be supported and/or stabilized in a variety of other ways, in addition to or in lieu of those noted above.

Figure 27:
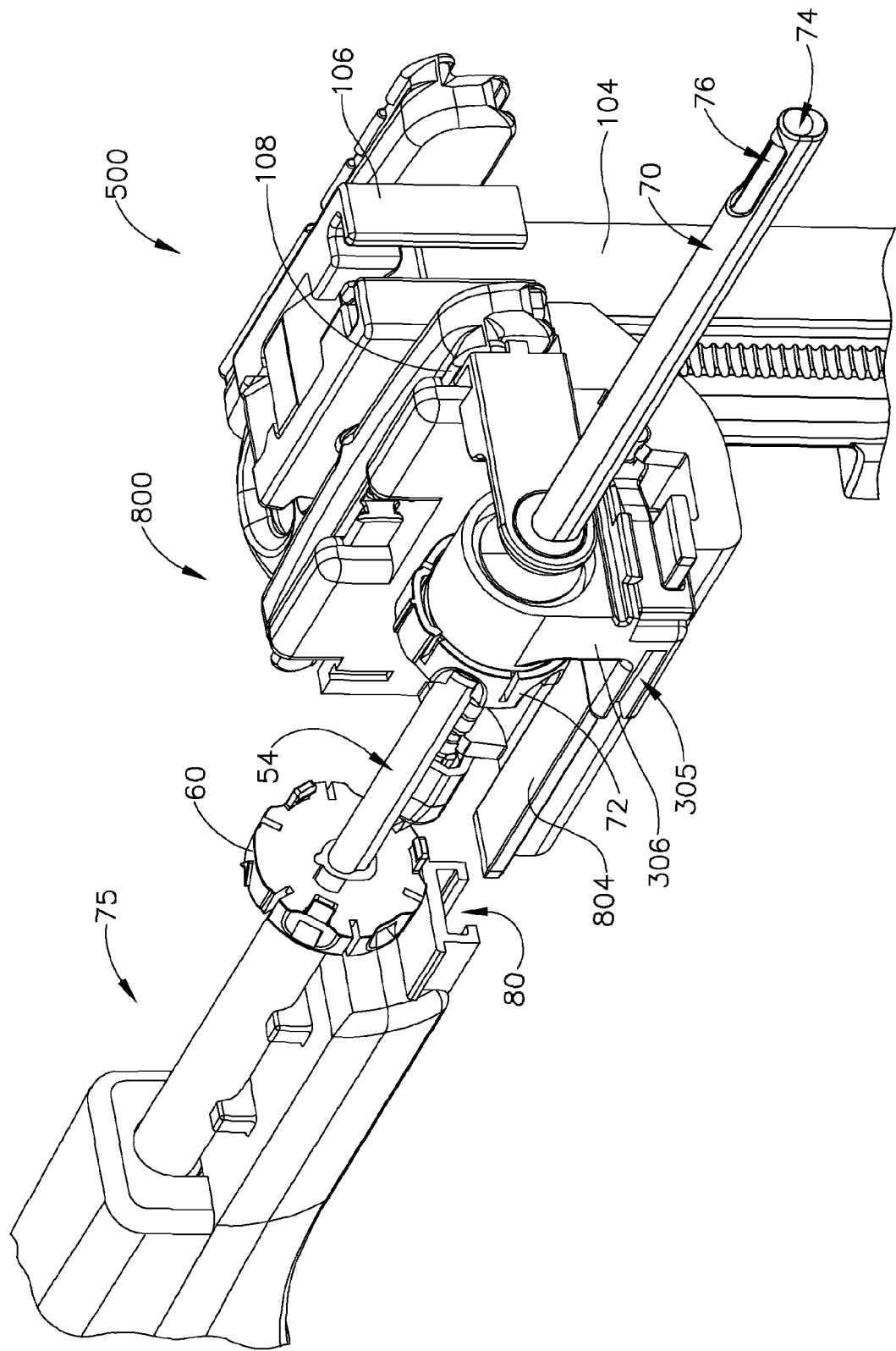
FIG. 27 shows a partial perspective view of another exemplary biopsy probe in a preliminary stage of engagement with an exemplary targeting set.
Figure 28:
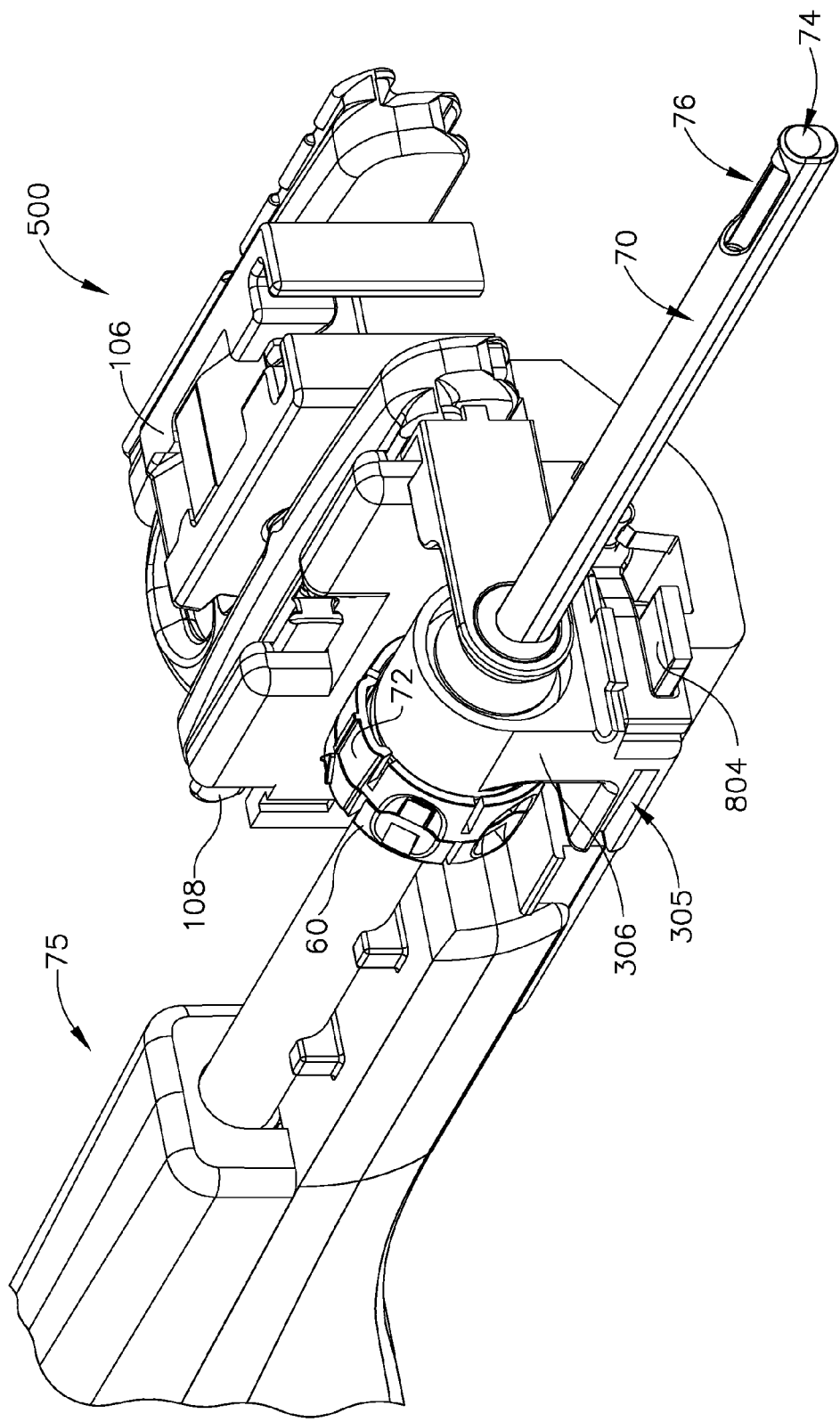
FIG. 28 shows a partial perspective view of the biopsy probe and targeting set of FIG. 27, in a subsequent stage of engagement.

As one mere example of how a biopsy device (75) may be otherwise supported, FIGS. 27-28 show a biopsy device (75) that lacks mounting arms (81) yet has a mounting recess (80). As shown, as biopsy device (75) is advanced distally, rail (804) enters recess (80). Biopsy device (75) continues to be advanced until thumbwheel (60) couples with thumbwheel (72). Biopsy device (75) is then supported by cradle (800) and pedestal (500). Despite the absence of mounting arms (81), biopsy device (75) still has various areas of engagement for support and stabilization in this example. In particular, biopsy device (75) may be supported and/or stabilized at least in part by engagement between the following components: needle (54) with cannula (70), thumbwheel (60) with thumbwheel (72), and recess (80) with rail (804). It should also be understood that engagement may be provided in several stages as biopsy device (75) is advanced toward cannula mount (306). For instance, in the present example, needle (54) engages cannula (70) first. Then recess (80) engages rail (804) as biopsy device is advanced further. Finally, thumbwheel (60) engages thumbwheel (72) as advancement of biopsy device (75) is completed. Of course, biopsy device (75) may be supported and/or stabilized in a variety of other ways, in addition to or in lieu of those noted above.

It should also be understood that, upon coupling of thumbwheels (60, 72) (or at any other suitable time or stage), needle (54) and cannula (70) may be rotated concomitantly. For instance, a user may manually rotate thumbwheel (62) of biopsy device (50). Such rotation may be communicated along a shaft (not shown) or other component to thumbwheel (62), which may in turn communicate such rotation to thumbwheel (72). A secure engagement between thumbwheel (72) and cannula (70) may further communicate such rotation to cannula (70). Of course there are a variety of other ways in which rotation may be communicated from a biopsy device (50, 75) to a targeting cannula (70).

Furthermore, those of ordinary skill in the art will appreciate that, while the examples depicted in FIGS. 25-28 include targeting cannulas (70) and biopsy devices (50, 75) that have an integral needle (54), similar methods of engagement may be provided for a biopsy device (10) that lacks an integral needle (54). For instance, biopsy device (10) shown in FIGS. 1-2 may include mounting arms (81) or similar features. Similarly, needle mount (506) may include recesses (305) that complement such mounting arms (81). Still other ways in which the teachings herein may be combined and interchanged among various examples will be apparent to those of ordinary skill in the art in view of the teachings herein.

V. Exemplary Multi-Orientation Mounting of Targeting Cradle and Cannula Mount

Figure 29A:
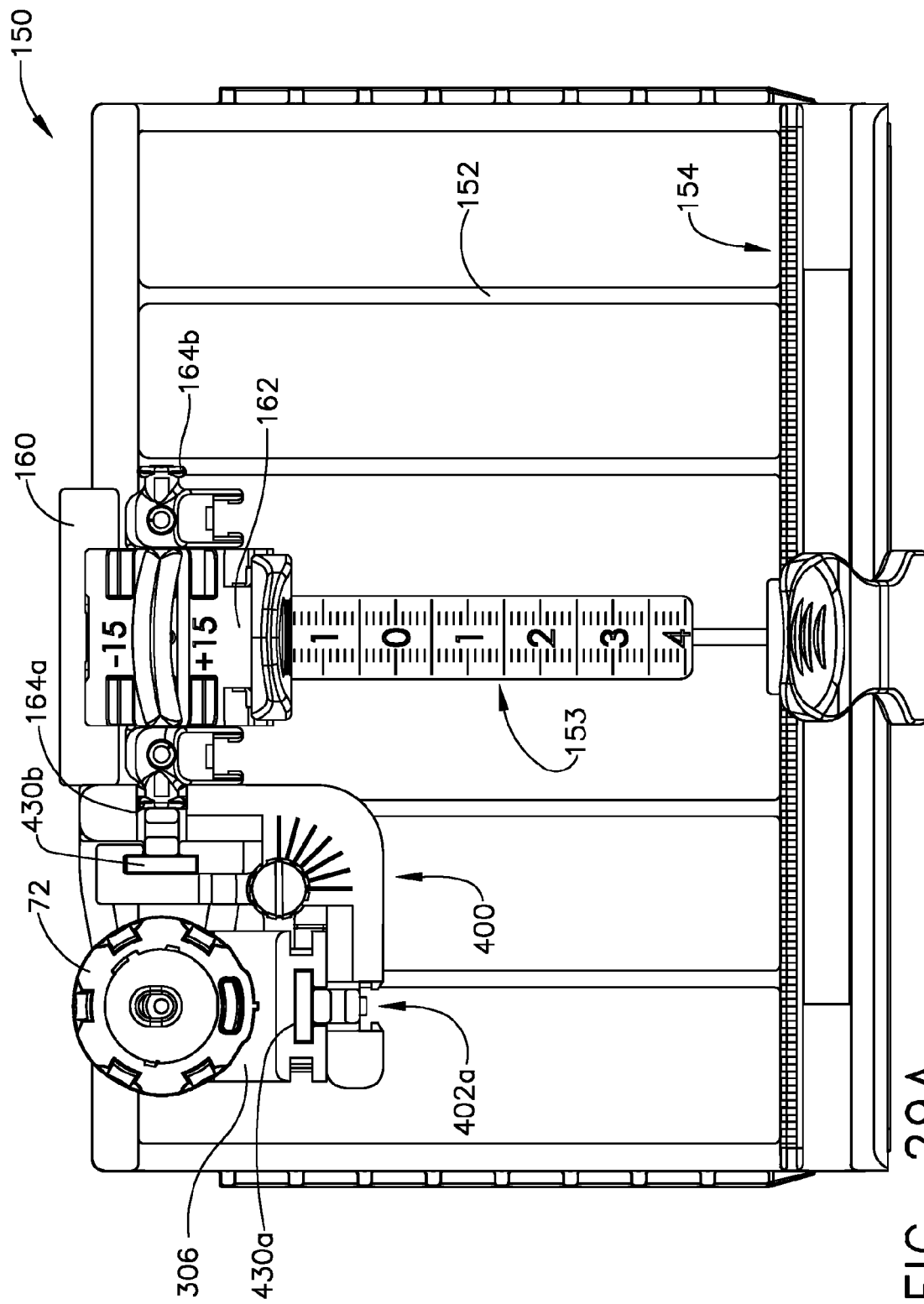
FIGS. 29A through 29H are a series of end views, showing various configurations in which a targeting set may be provided.

FIGS. 29A-29H show various orientations that may be achieved with a targeting grid assembly (150), cradle (400), and cannula mount (306). For instance, cradle (400) may be engaged with targeting grid assembly (150) in a variety of ways. Similarly, cannula mount (306) may be engaged with cradle (400) in a variety of ways. Such various combinations and arrangements may be desirable to optimize positioning in view of size or space constraints, access to thumbwheel (62), and/or in view of any other considerations. In particular, as shown in FIG. 29A, recess (402b) of cradle (400) may be engaged with rail (164a) of carriage (162); while cannula mount (306) is engaged with rail (403a) of cradle (400). A biopsy device (10, 50, 75) may be engaged with either rail (430a, 430b) of cradle (400) in this example.

Figure 29B:
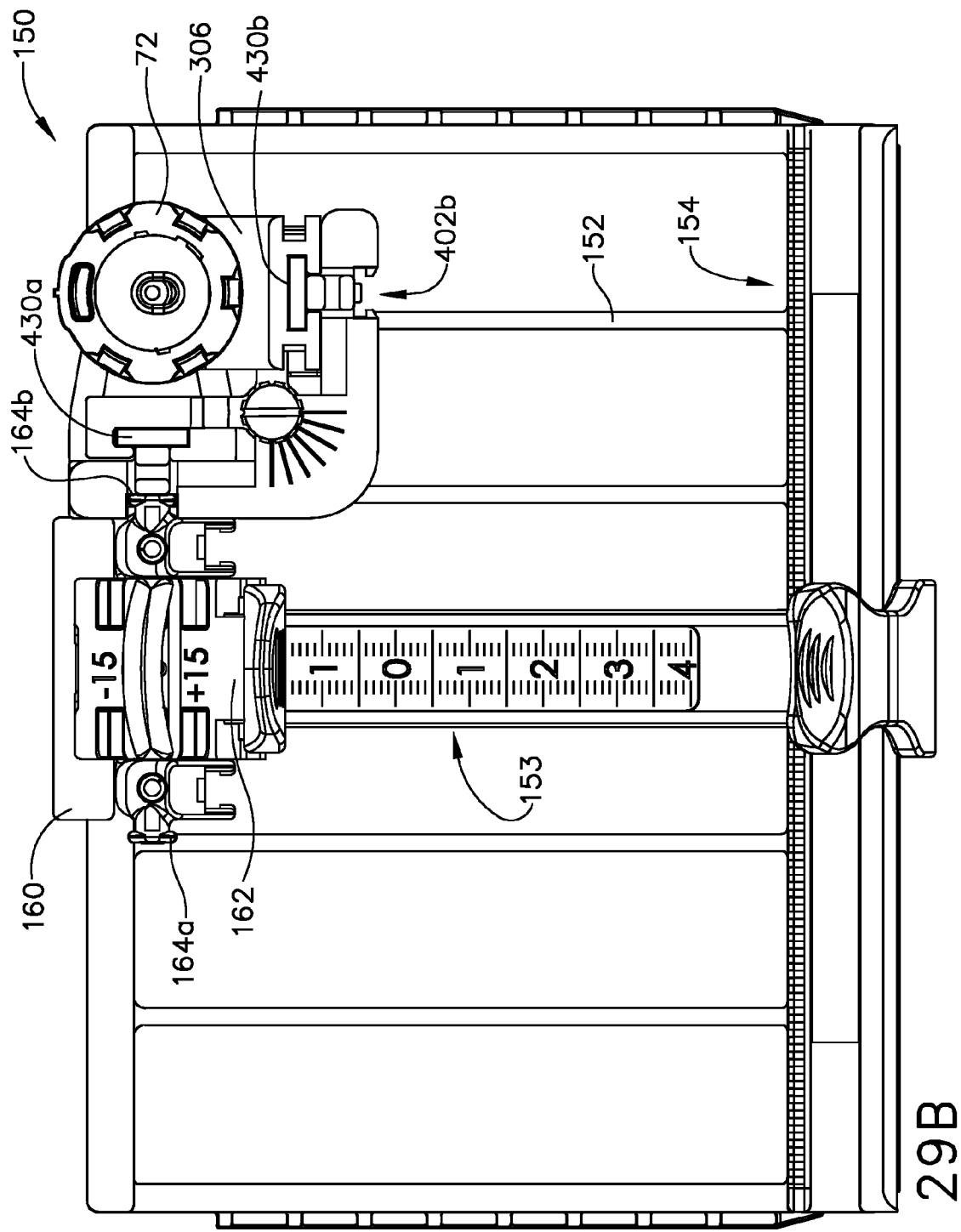

As shown in FIG. 29B, recess (402a) of cradle (400) may be engaged with rail (164b) of carriage (162); while cannula mount (306) is engaged with rail (430b) of cradle (400). A biopsy device (10, 50, 75) may be engaged with either rail (430a, 430b) of cradle (400) in this example.

Figure 29C:
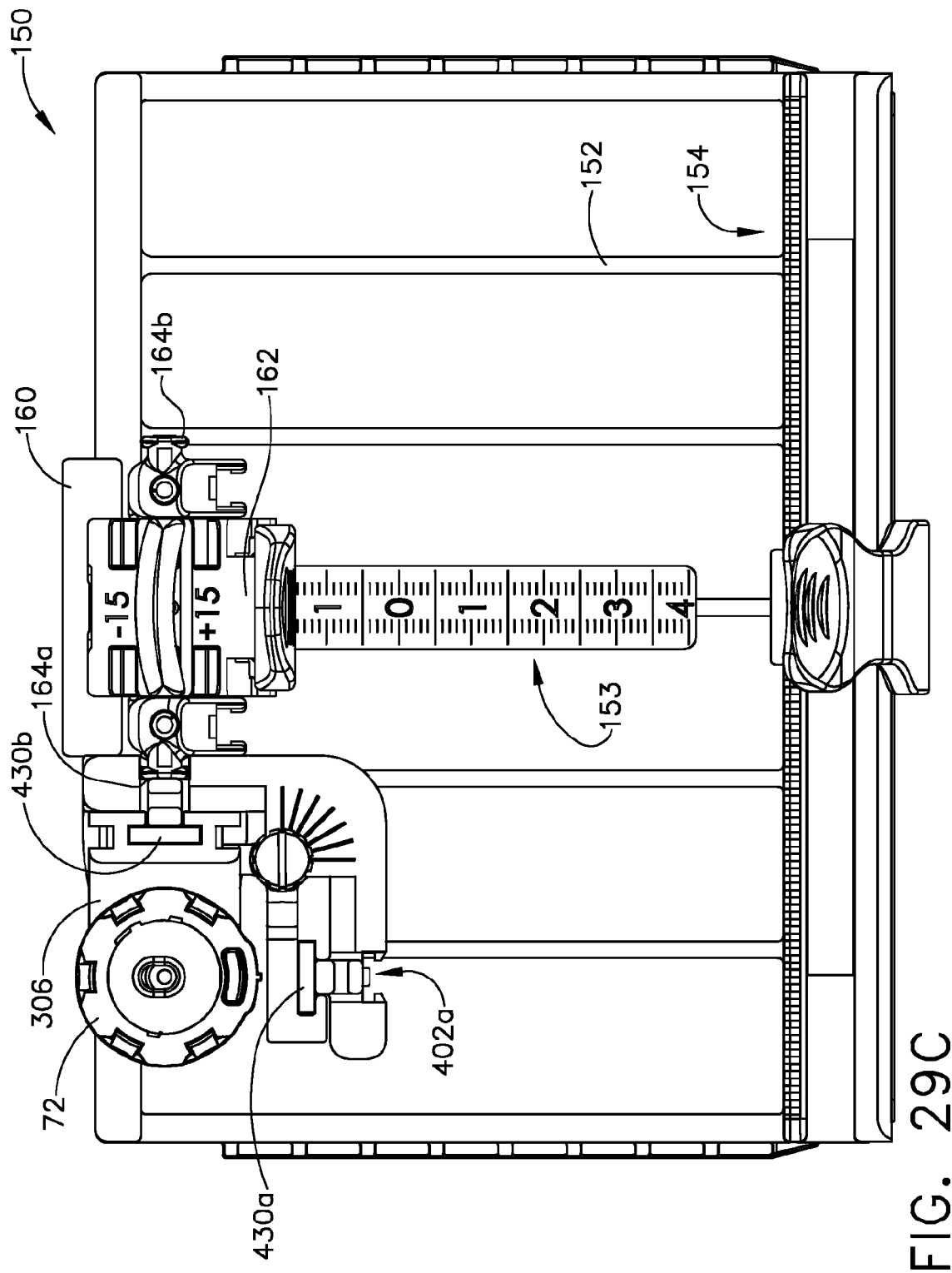

As shown in FIG. 29C, recess (402b) of cradle (400) may be engaged with rail (164a) of carriage (162); while cannula mount (306) is engaged with rail (430b) of cradle (400). A biopsy device (10, 50, 75) may be engaged with either rail (430a, 430b) of cradle (400) in this example.

Figure 29D:
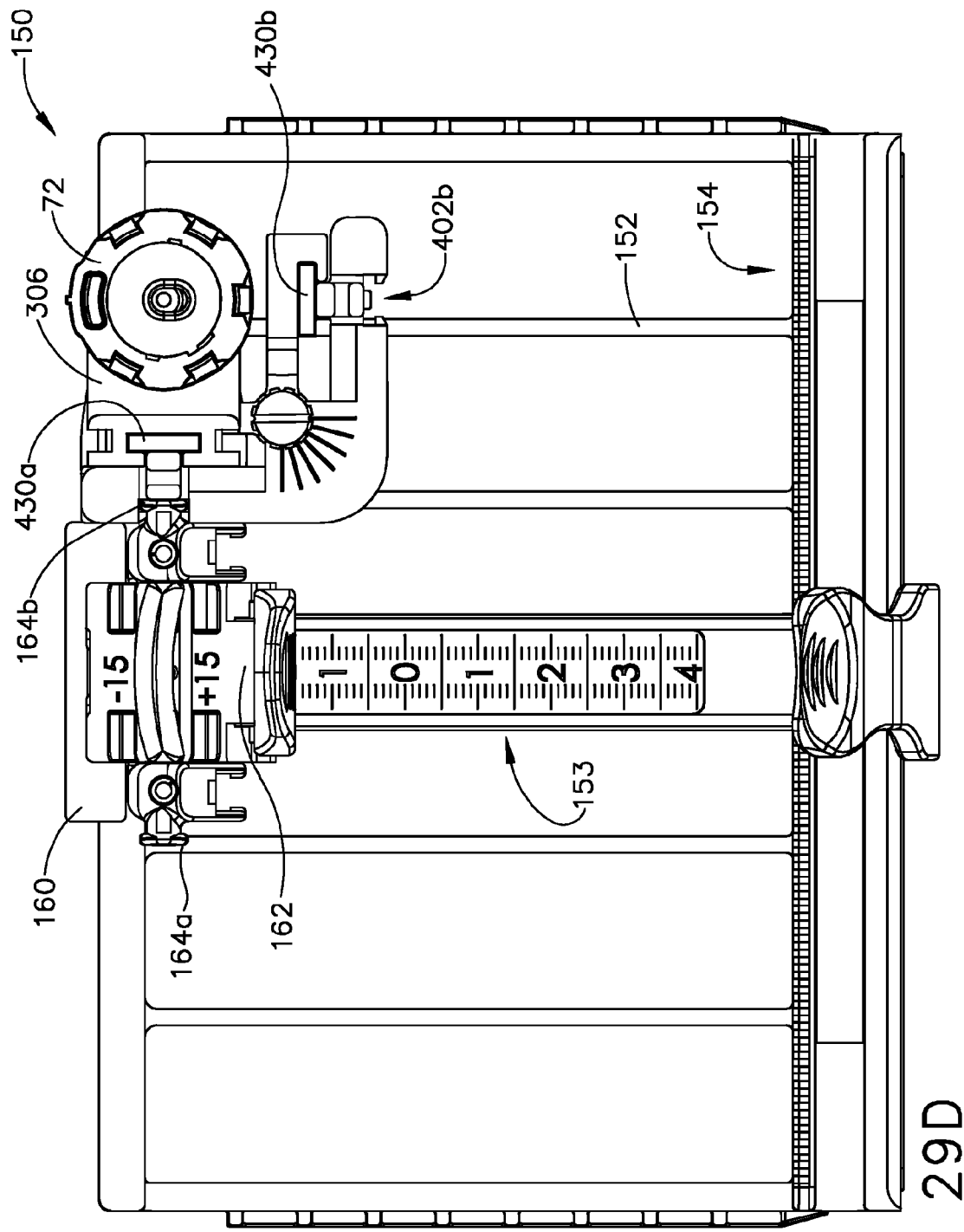

As shown in FIG. 29D, recess (402a) of cradle (400) may be engaged with rail (164b) of carriage (162); while cannula mount (306) is engaged with rail (430a) of cradle (400). A biopsy device (10, 50, 75) may be engaged with either rail (430a, 430b) of cradle (400) in this example.

Figure 29E:
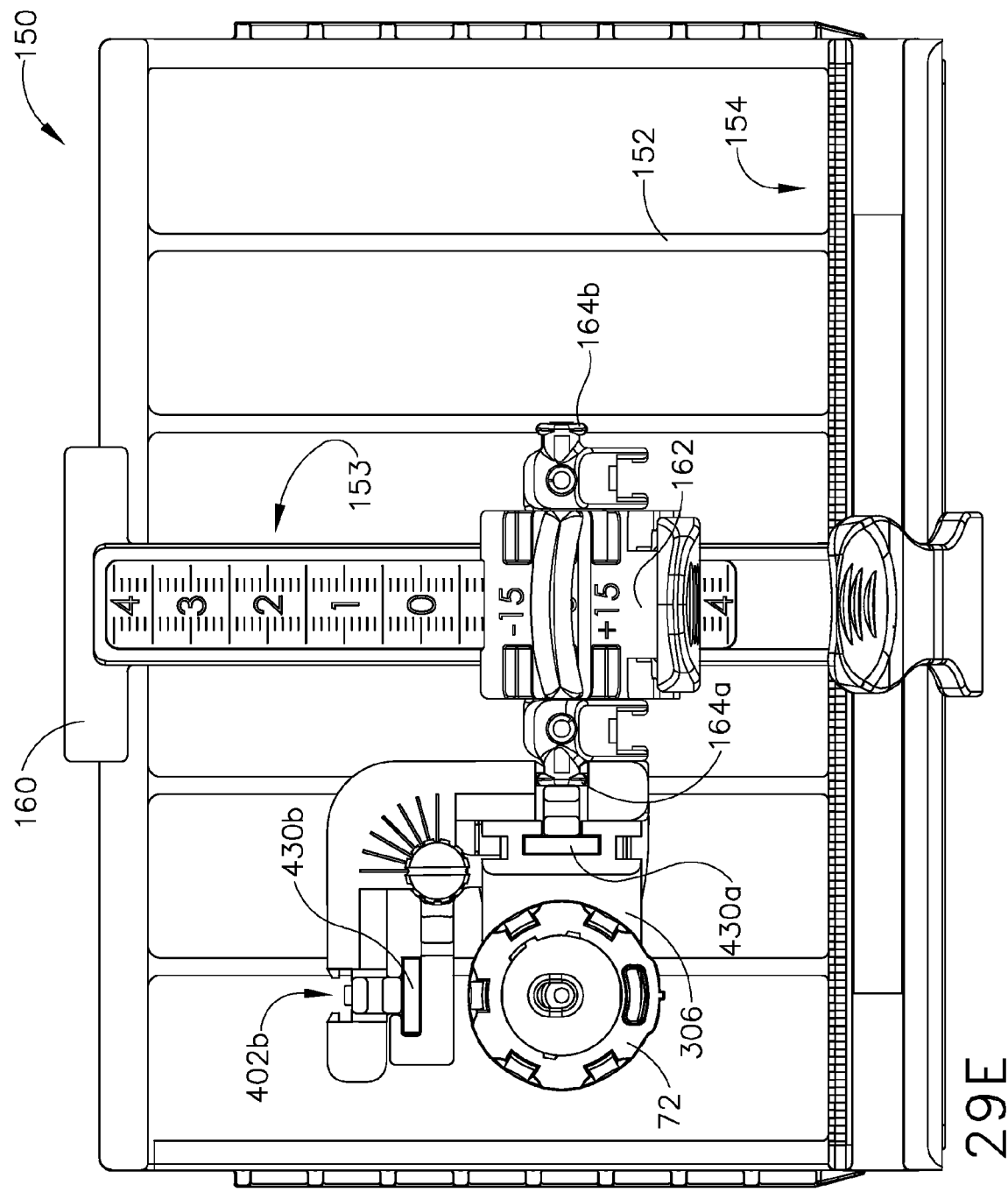

As shown in FIG. 29E, recess (402a) of cradle (400) may be engaged with rail (164a) of carriage (162); while cannula mount (306) is engaged with rail (430a) of cradle (400). A biopsy device (10, 50, 75) may be engaged with either rail (430a, 430b) of cradle (400) in this example.

Figure 29F:
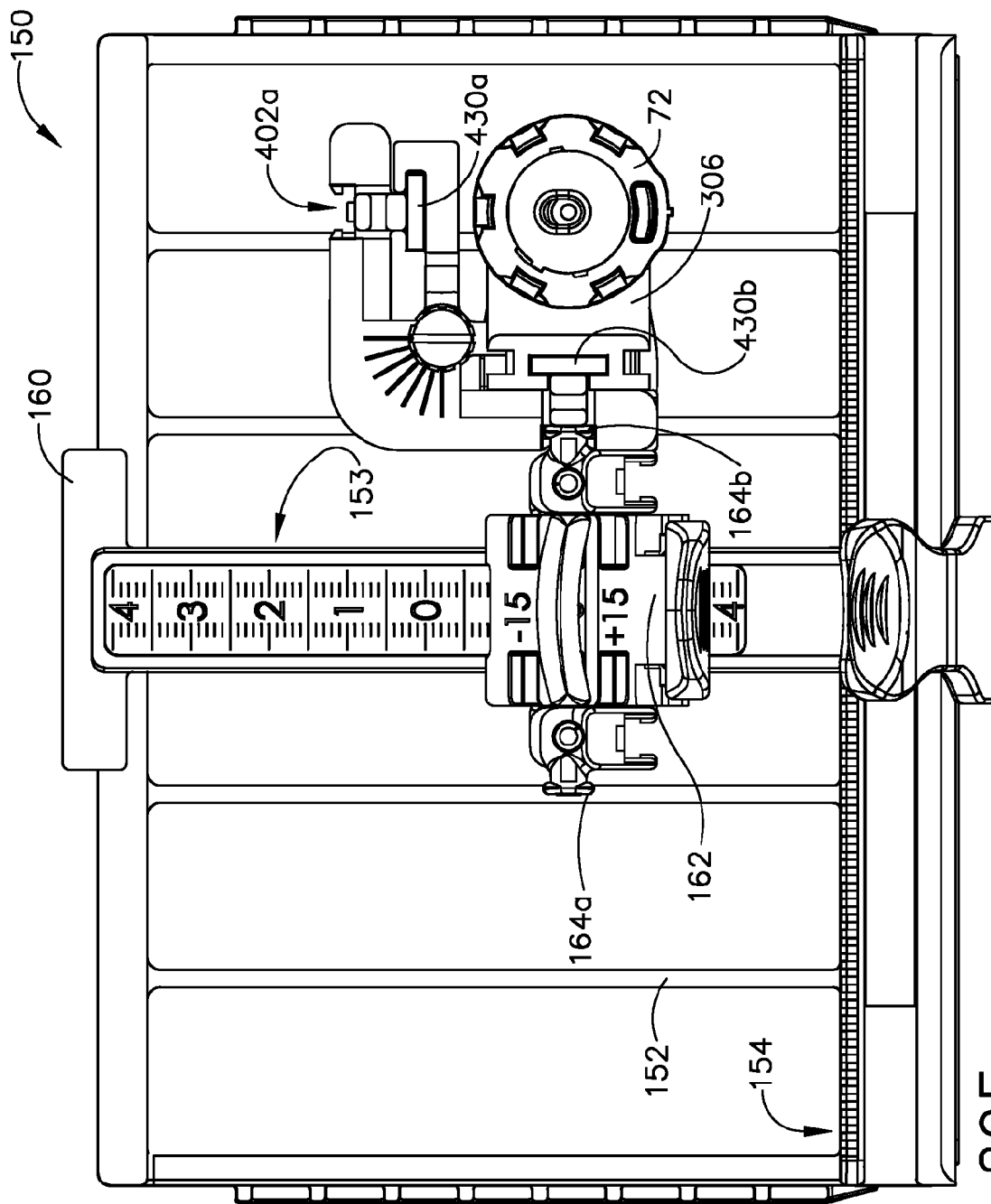

As shown in FIG. 29F, recess (402b) of cradle (400) may be engaged with rail (164b) of carriage (162); while cannula mount (306) is engaged with rail (430b) of cradle (400). A biopsy device (10, 50, 75) may be engaged with either rail (430a, 430b) of cradle (400) in this example.

Figure 29G:
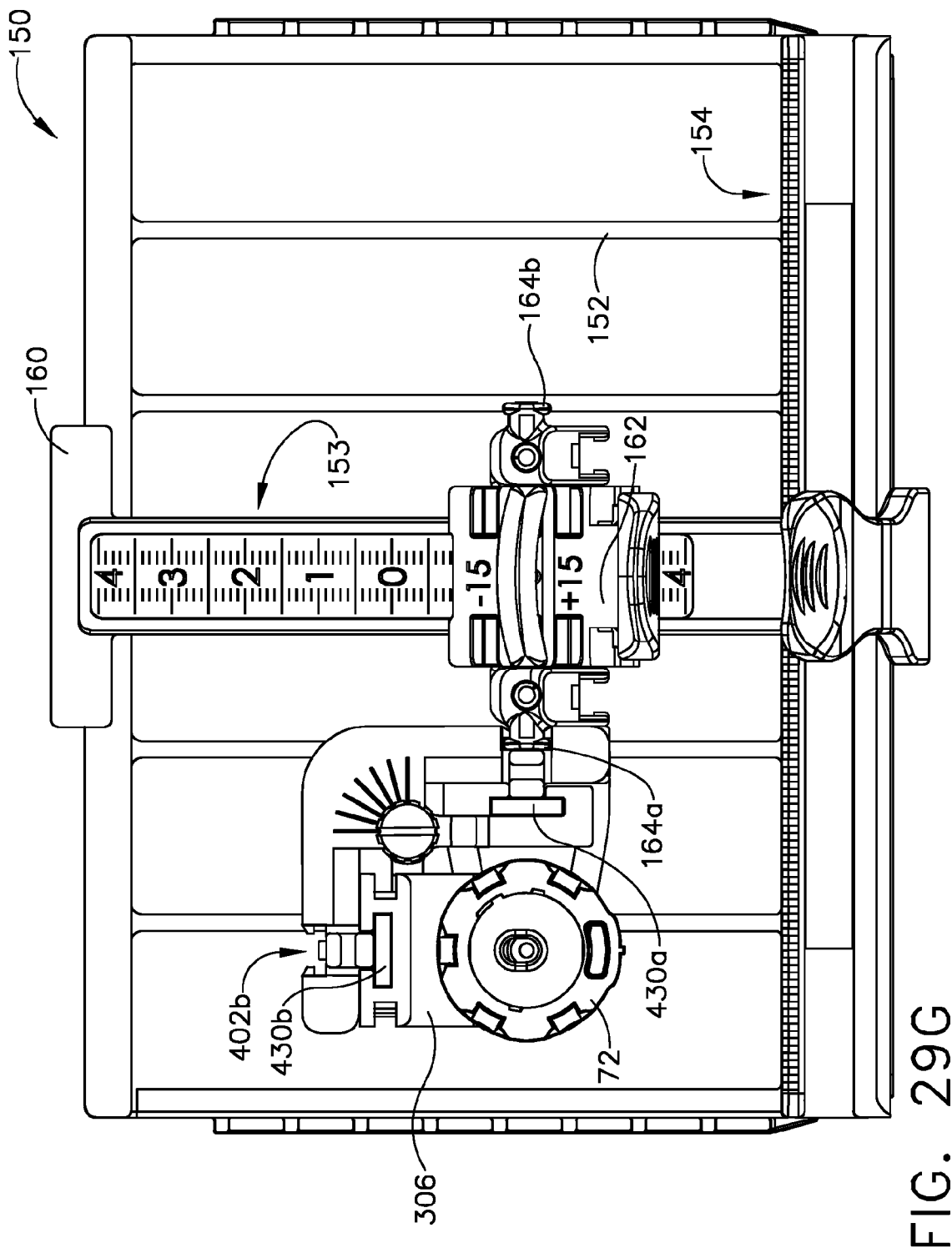

As shown in FIG. 29G, recess (402a) of cradle (400) may be engaged with rail (162a) of carriage (162); while cannula mount (306) is engaged with rail (430b) of cradle (400). A biopsy device (10, 50, 75) may be engaged with either rail (430a, 430b) of cradle (400) in this example.

Figure 29H:
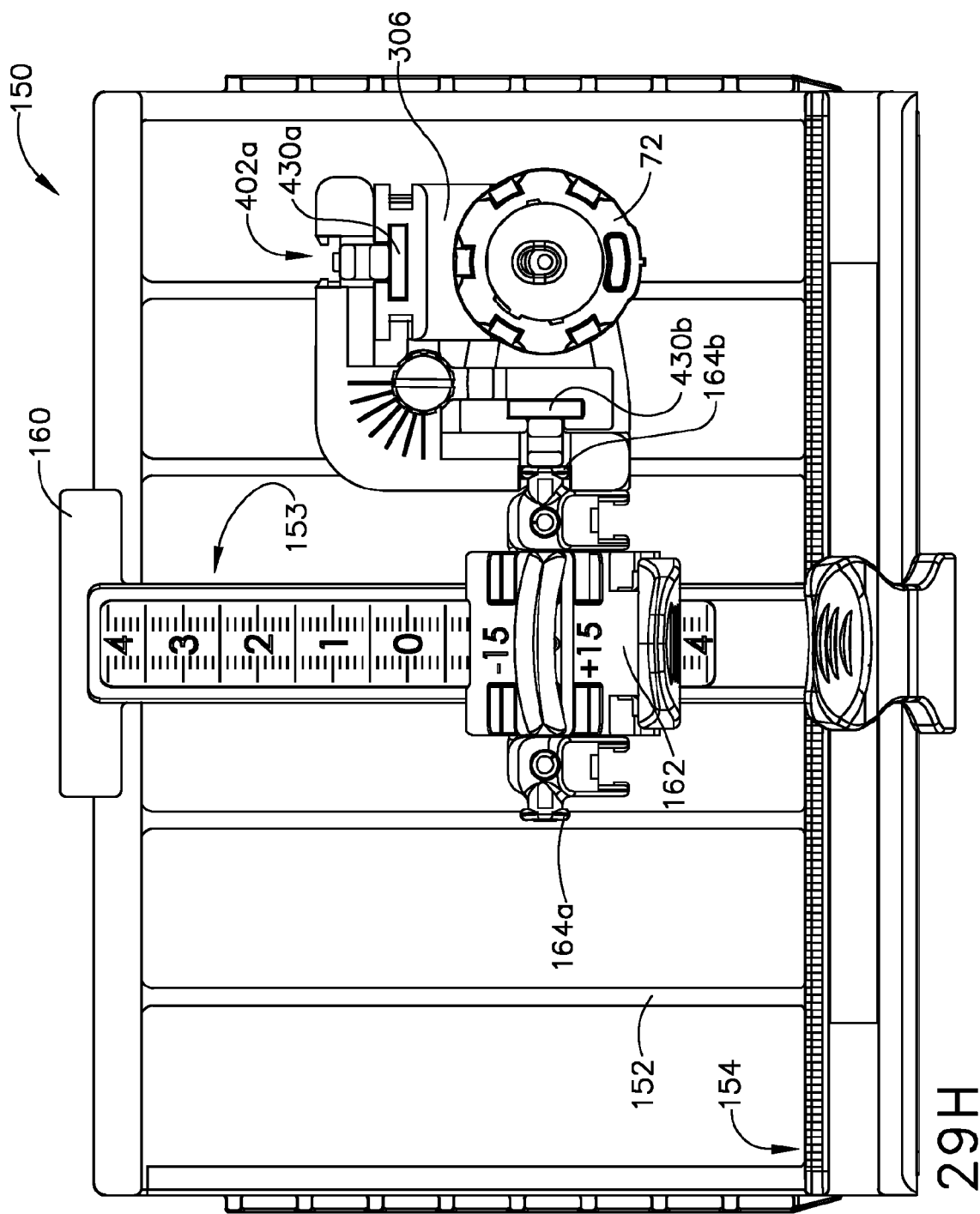

As shown in FIG. 29H, recess (402b) of cradle (400) may be engaged with rail (164b) of carriage (162); while cannula mount (306) is engaged with rail (430a) of cradle (400). A biopsy device (10, 50, 75) may be engaged with either rail (430a, 430b) of cradle (400) in this example.

While the examples depicted in FIGS. 29A-29H include targeting grid assembly (150), it should be understood that the same various orientations and combinations may be achieved using a platform (100) or other mounting structure. Similarly, while cradle (400) is depicted in FIGS. 29A-29H, it should be understood that various orientations and combinations may be achieved using a variety of other cradles (200, 300, 500, 600, 700, 800). Likewise, while cannula mount (306) is depicted in FIGS. 29A-29H, it should be understood that various orientations and combinations may be achieved using a needle mount (506) or other structures. Still other combinations and variations will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times.

Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A targeting set for use with a biopsy device, wherein the biopsy device comprises a body and a needle extending from the body, wherein the targeting set comprises:
   (a) a vertical member;
   (b) a carriage, wherein the carriage is vertically movable with respect to the vertical member, wherein the carriage has a first elongate mounting rail; and
   (c) a cradle, wherein the cradle comprises:
      (i) a first mounting arm, wherein the first mounting arm has an elongate recess configured to receive the first elongate mounting rail, wherein the elongate recess is disposed on an outer surface of the first arm and spaced away from an end of the first arm, wherein the first mounting arm further has a biopsy device mounting feature, wherein the biopsy device mounting feature is configured to removably couple with a portion of the biopsy device, and
      (ii) a second mounting arm, wherein the second mounting arm has an elongate recess configured to receive the first elongate mounting rail, wherein the elongate recess is disposed on an outer surface of the second arm and spaced away from an end of the second arm, wherein the second mounting arm further has a biopsy device mounting feature, wherein the biopsy device mounting feature is configured to removably couple with a portion of the biopsy device, wherein the second mounting arm is perpendicular to the first mounting arm;
      wherein the first mounting arm is symmetric with the second mounting arm such that the first mounting arm corresponds in size and shape to the second mounting arm.

2. The targeting set of claim 1, further comprising a grid, wherein the vertical member is coupled with the grid.

3. The targeting set of claim 1, further comprising a platform base, wherein the vertical member extends from the platform base.

4. The targeting set of claim 1, wherein the carriage has a second elongate mounting rail.

5. The targeting set of claim 4, wherein the elongate recess of the first mounting arm and the elongate recess of the second mounting arm are each configured to selectively receive either the first elongate mounting rail of the carriage or the second elongate mounting rail of the carriage.

6. The targeting set of claim 1, wherein the first mounting arm and the second mounting arm each comprise a snap fit feature adjacent to the respective elongate recess, wherein the snap fit feature is configured to restrict longitudinal movement of the respective mounting arm relative to the first elongate mounting rail.

7. The targeting set of claim 6, wherein the snap fit feature comprises a resilient arm and a protrusion extending from the resilient arm, wherein the protrusion is configured to engage a recess formed on the first elongate mounting rail.

8. The targeting set of claim 1, wherein the biopsy device mounting feature of the first mounting arm comprises an elongate recess.

9. The targeting set of claim 1, wherein the biopsy device mounting feature of the first mounting arm comprises a rail.

10. The targeting set of claim 9, wherein the biopsy device mounting feature of the second mounting arm comprises a recess.

11. The targeting set of claim 9, wherein the rail has a T-shaped cross section.

12. The targeting set of claim 1, further comprising a targeting cannula coupled with the mount, wherein the targeting cannula is configured to receive the needle of the biopsy device.

13. A targeting set for use with a biopsy device, wherein the biopsy device comprises a body and a needle extending from the body, wherein the targeting set comprises:
   (a) a vertical member;
   (b) a carriage, wherein the carriage is vertically movable with respect to the vertical member, wherein the carriage has a first elongate mounting rail;
   (c) a cradle, wherein the cradle comprises:
      (i) a first mounting arm, wherein the first mounting arm has an elongate recess configured to receive the first elongate mounting rail, wherein the first mounting arm further has a biopsy device mounting feature, wherein the biopsy device mounting feature is configured to removably couple with a portion of the biopsy device, and
      (ii) a second mounting arm, wherein the second mounting arm has an elongate recess configured to receive the first elongate mounting rail, wherein the second mounting arm further has a biopsy device mounting feature, wherein the biopsy device mounting feature is configured to removably couple with a portion of the biopsy device, wherein the second mounting arm is perpendicular to the first mounting arm;
   (d) a mount, wherein the mount is configured to couple with the biopsy device mounting feature of the first mounting arm or the second mounting arm, wherein the mount is movable longitudinally along the biopsy device mounting feature of the first arm or the second arm; and
   (e) a z-stop feature configured to engage with the biopsy device mounting feature of the first mounting arm or the second mounting arm and operable to selectively restrict the longitudinal distance to which the mount may be moved along the biopsy device mounting feature of the first mounting arm or the second mounting arm, wherein the z-stop feature comprises a first arm and a second arm, wherein the first arm is configured to align with one of the first mounting arm or the second mounting arm and the second arm is configured to align with the other of the first mounting arm or the second mounting arm.

* * * * *

UNITED STATES PATENT AND TRADEMARK OFFICE
CERTIFICATE OF CORRECTION

PATENT NO. : 8,460,206 B2
APPLICATION NO. : 12/337872
DATED : June 11, 2013
INVENTOR(S) : Parihar et al.

Page 1 of 1

It is certified that error appears in the above-identified patent and that said Letters Patent is hereby corrected as shown below:

In the Claims:

Column 24, Claim 12, line 24, reads "...the mount..."; which should be deleted and replaced with "...the cradle...."

Column 24, Claim 13, line 38, reads "...a biopsy device mounting feature..."; which should be deleted and replaced with "...a first biopsy device mounting feature...."

Column 24, Claim 13, line 39, reads "...the biopsy device mounting feature..."; which should be deleted and replaced with "...the first biopsy device mounting feature...."

Column 24, Claim 13, lines 45-46, read "...a biopsy device mounting feature..."; which should be deleted and replaced with "...a second biopsy device mounting feature...."

Column 24, Claim 13, line 46, reads "...the biopsy device mounting feature..."; which should be deleted and replaced with "...the second biopsy device mounting feature...."

Column 24, Claim 13, line 54, reads "...the first arm or the second arm..."; which should be deleted and replaced with "...the first mounting arm or the second mounting arm...."

Column 24, Claim 13, line 58, reads "...the longitudinal distance..."; which should be deleted and replaced with "...a longitudinal distance...."

Signed and Sealed this
Twentieth Day of August, 2013

Teresa Stanek Rea
*Acting Director of the United States Patent and Trademark Office*